(12) United States Patent
Goel et al.

(10) Patent No.: US 10,190,135 B2
(45) Date of Patent: Jan. 29, 2019

(54) CHIMERIC POST-TRANSCRIPTIONAL REGULATORY ELEMENT

(71) Applicant: Celltheon Corporation, Union City, CA (US)

(72) Inventors: Nikhil Goel, Union City, CA (US); Amita Goel, Union City, CA (US)

(73) Assignee: Celltheon Corporation, Union City, CA (US)

( * ) Notice: Subject to any disclaimer, the term of this patent is extended or adjusted under 35 U.S.C. 154(b) by 0 days.

(21) Appl. No.: 15/335,930

(22) Filed: Oct. 27, 2016

(65) Prior Publication Data

US 2017/0114363 A1   Apr. 27, 2017

Related U.S. Application Data

(60) Provisional application No. 62/246,841, filed on Oct. 27, 2015.

(51) Int. Cl.
*C12N 15/85* (2006.01)
*C07K 16/28* (2006.01)

(52) U.S. Cl.
CPC .......... *C12N 15/85* (2013.01); *C07K 16/2887* (2013.01); *C12N 2800/107* (2013.01); *C12N 2830/30* (2013.01); *C12N 2830/48* (2013.01); *C12N 2830/60* (2013.01)

(58) Field of Classification Search
None
See application file for complete search history.

(56) References Cited

U.S. PATENT DOCUMENTS

| 6,287,814 | B1 * | 9/2001 | Hope | C07K 14/005 |
| | | | | 435/375 |
| 2006/0019393 | A1 * | 1/2006 | Cannon | C07K 14/005 |
| | | | | 435/456 |
| 2015/0291975 | A1 * | 10/2015 | Minshull | A61K 31/00 |
| | | | | 800/15 |
| 2017/0051308 | A1 * | 2/2017 | Morgan | C07K 16/2803 |

FOREIGN PATENT DOCUMENTS

| WO | WO-2014070949 A1 * | 5/2014 | ......... A61K 48/0066 |
| WO | WO-2015157579 A2 * | 10/2015 | ............. A61K 31/00 |

OTHER PUBLICATIONS

Score result to Baltimore for SEQ No. 7 (Year: 2014).*
Score result to Caves for SEQ No. 3 (Year: 2015).*
Score result to Caves for SEQ No. 18 (Year: 2015).*
Intenational Search Report and Written Opinion of PCT/US2016/59151 dated May 5, 2017 (12 pages).
GenBank Accession K02715.1, Ground squirrel hepatitis virus (GSHV), complete genome [online] Feb. 10, 1994 [retrieved Jan. 24, 2017]. Availble on the internet: <http:"www.ncbi.nlm.hih.gov/nuccore/K02715>. Especially 2. (3 pages).

* cited by examiner

*Primary Examiner* — Catherine S Hibbert
(74) *Attorney, Agent, or Firm* — Sheppard Mullin Richter & Hampton LLP

(57) ABSTRACT

The present disclosure relates to chimeric post-transcriptional regulatory elements (PRE) and vectors useful for expressing a protein in a cell. The PRE contains alpha, beta and optionally gamma subelements selected from different native PRE sequences and are discovered to be more potent than their native counterparts.

6 Claims, 8 Drawing Sheets

Specification includes a Sequence Listing.

```
HPREα    GTTGCTCGGCAACGGCCTGGTCTGTGCCAAGTGTTTGCTGACGCAACCCCCACTGGTTGG
BPREα    GTTATCAGGCAGAAGCGGGCAATCTGCCAGGTGTTTGCTGACGCAACCCCCACTGGTTGG
ASPREα   GTTGCCAGGCAACGTGGCGTGGTGTGCTCTG---TGTCTGACGCAACCCCCACTGGTTGG
WPREα    GTTGTCAGGCAACGTGGCGTGGTGTGCACTGTGTTTGCTGACGCAACCCCCACTGGTTGG
GSPREα   GTTGCCAGACAACGTGGTGTGGTGTGCTCTGTGTTTGCTGACGCAACTCCCACTGGTTGG
         **     *  **       *    *  ***     *    * ********** ***********

HPREα    GGCTTGGCCATAGGCCATCAGCGCA------TGCGTGGAACCTTTGTGTCTCCTCTGCCG
BPREα    GGCCTGGTTAATCATTCCTCCGCATGGTTGCGCAGGGGACGGTTTCCCCGCCCCTTGCCT
ASPREα   GGCATTTGCACCACCTATCAACTCA------TTTCCCCGACGGGCGCTTTTGCCCTGCCG
WPREα    GGCATTGCCACCACCTGTCAGCTCC------TTTCCGGGACTTTCGCTTTCCCCCTCCCT
GSPREα   GGCATTTGCACCACCTGTCAACTCA-------TTTCCGGTACTTTCGGTTTCTCACTTCCG
         ***  *     *                                    *   *   * **

HPREα    ATCCATACTGCGGAACTCCTAGCCGCTTGTTTTGCTCGCAGCAGGTCTGGAGCAAACCTC
BPREα    ATCCATTGCGCGGAACTTATTGCCGCCTGCCTTGCTCGCCGCTGGACGGGAGCTCGGGTT
ASPREα   ATCGCCACCGCGGACGTCATCGCCGCCTGCCTTGCTCGCTGCTGGACAGGAGCTCGGCTG
WPREα    ATTGCCACGGCGGAACTCATCGCCGCCTGCCTTGCCCGCTGCTGGACAGGGGCTCGGCTG
GSPREα   ATTGCTACCGCGGAGCTTATAGCCGCCTGCCTTGCTCGCTGCTGGACAGGAGCTCGGTTG
         **      ***** *  * ***** ** **** ** *** ** ** * ** **     *

HPREα    ATCGGGACCGACAATTCTGTCGTACTCTCCCGCAAGTATACATCGTTTCCATGGCTGCTA
BPREα    ATTGGAACTGACAATTCCATTGTGGCTTCGGGAAAGCGGACATCTTTCCCATGGCTGCTC
ASPREα   TTGGGCACTGACAACTCCGTGGTTCTTTCGGGCAAACTGACTTCCTATCCATGGCTGCTC
WPREα    TTGGGCACTGACAATTCCGTGGTGTTGTCGGGGAAGCTGACGTCCTTTCCATGGCTGCTC
GSPREα   TTGGGCACTGATAACTCCGTGGTCCTCTCCGGTAAGCTAACTTCGTTTCCATGGCTGCTC
           * **  ** ** **  **   *  *  **       **   **  *  **********

HPREα    GGCTGTGCTGCCAACTGGTACCTGCGC--
BPREα    GGCTGCGTTGCCAACTGGATGCTTCGGGC
ASPREα   GCCTGTGTTGCCAACTGGATTCTTCGC--
WPREα    GCCTGTGTTGCCACCTGGATTCTGCGC--
GSPREα   GCCTGTGTTGCCAACTGGATTCTTCGC--
         * *** * ***** ****   ** **
```

FIG. 1

```
HPREβ    GGGACGTCCTTTGTTTACGTCCCGTCGGCGCTGAATCCCGCGGACGACCCCTCCCGGGGC
BPREβ    -GAACGTCGTTCTGCTTCGTCCCCTCTGCATTGAATCCGGCGGACGCCCCGTCGCGCGGA
GSPREβ   GGGACGTCCTTCTGTTACGTCCCCTCCGCGGACAACCCAGCGGACCTTCCGTCTCGGGGA
WPREβ    GGGACGTCCTTCTGCTACGTCCCTTCGGCCCTCAATCCAGCGGACCTTCCTTCCCGCGGC
ASPREβ   GGGACGTCGTTCTGCTACGTCCCTTCGGCAGCGAATCCGGCGGACCTGCCGTCTCGAGGC
          * ***** **    * ****** ** **     ** **  ******   ** ** ** **

HPREβ    CGCTTGGGGCTCTACCGCCCGCTTCTCCGTCTGCCGTACCGTCCGACCACGGGGCGCACC
BPREβ    CTGCTCGGCATTCCCGTCGCGCCGCCGCCTCTCCCGTTCCGACCTTCTACGGGCCGCACG
GSPREβ   CTTCTGCCGGCTCTCCGTCCTCTGCCGCTTCTGCGTTTTCGTCCGGTCACCAAGCGGATA
WPREβ    CTGCTGCCGGCTCTGCGGCCTCTTCCGCGTCTTCGCCTTCGCCCTCAGACGAGTCGGATC
ASPREβ   CTTCTGCCGGCTCTGCATCCCGTGCCGACTCTCCGCTTCCGTCCGCAGCTGAGTCGCATC
          *   *         *    *    * ***  *    ** **            ** *

HPREβ    TCTCTTTACGCGGACTCCCCGTCTGTGCCTTCTCATCTGCCGGACCGTGTGC
BPREβ    TCACTCTTCGCCGTCTCCCCATCTG---------------------------
GSPREβ   TCCCTGTGGGCCGCCTCCCCGCCTG---------------------------
WPREβ    TCCCTTTGGGCCGCCTCCCCGCCTGGGATC----------------------
ASPREβ   TCCCTTTGGGCCGCCTCCCCGCCTG---------------------------
          **  ** *  ** * ****** ***
```

FIG. 2

```
BPREγ     AACAAGCCTTTGGATTGGAAAATCCTTCAGCGCATTACGGGTCTCCTGGGGTTTCTTGCA
ASPREγ    ----AACCTTTAGATTATAAAATCTGTGAAAGGTTAACAGGCATTCTGAATTATGTTGCT
WPREγ     AATCAACCTCTGGATTACAAAATTTGTGAAAGATTGACTGGTATTCTTAACTATGTTGCT
GSPREγ    AATCAACCCTTAGATTATAAAATATGTGAAAGGTTGACGGGCATTCTTAATTATGTTGCT
           *  **  *  ****  *****   *  *   *  * **  **    *  **     *  *  ****

BPREγ     CCCTTCACGACCTGTGGCTATCCAGCCCTAATGCCTTTGTACCATGCCATTACCCGGCGC
ASPREγ    CCTTTTACTAAATGTGGTTATGCTGCTCTCCTTCCTTTGTATCAAGCTACTTCGC---GT
WPREγ     CCTTTTACGCTATGTGGATACGCTGCTTTAATGCCTTTGTATCATGCTATTGCTTCCCGT
GSPREγ    CCTTTTACCAAATGTGGTTATGCTGCTTTACTGCCTTTATATCAAGCTATTGCTTCTCAT
           ** **  **      ***** **   * **   *   * ***** **  **  **   *  *

BPREγ     CAGGCCTTAAAAATTTCCTGGCCCTTTAAGACCTTTCTTTACAGCCTGTACAAGCAACCT
ASPREγ    ACGGCATTTGTGTTTTCTTCTCTCTACCACAGCTGGTTGCTGTCCCTTTATGCTGAGTTG
WPREγ     ATGGCTTTCATTTTCTCCTCCTTGTATAAATCCTGGTTGCTGTCTCTTTATGAGGAGTTG
GSPREγ    ACTGCTTTTGTTTCTCCTCCTTATATAAAAACTGGTTACTGTCACTTTATGGTGAGTTG
             **  **       *   ** *         *   *   **   *      **  **       *

BPREγ     TTGCCC
ASPREγ    TGGCCT
WPREγ     TGGCCC
GSPREγ    TGGCCC
           *  ***
```

FIG. 3

CHIMERIC POST-TRANSCRIPTIONAL REGULATORY ELEMENT

CROSS-REFERENCE TO RELATED APPLICATIONS

This application claims the benefit under of 35 U.S.C. § 119(e) of U.S. Provisional Application 62/246,841, filed on Oct. 27, 2015, the content of which is hereby incorporated by reference.

SEQUENCE LISTING

The instant application contains a Sequence Listing which has been submitted electronically in ASCII format and is hereby incorporated by reference in its entirety. Said ASCII copy, created on Nov. 18, 2016, is named 45AH-221512-US_SL.txt and is 26,330 bytes in size.

BACKGROUND

Transcription of gene sequences (i.e., production of mRNA) is controlled at a number of different levels. Transcription initiation sites, or promoters, have different strengths, and the frequency of initiation of transcription of a given gene can also be augmented by enhancer sequences. Pausing during transcription can influence the rate of transcription and, hence, the amount of transcript produced in a given time period. Rates of pre-mRNA splicing, polyadenylation and cleavage can also influence the level of mRNA produced by a transcription unit. In addition, sequences within a mRNA molecule can regulate its transport from the nucleus to the cytoplasm, and its rate of turnover (i.e., its cytoplasmic stability).

Certain sequences within mRNA molecules that regulate the cytoplasmic accumulation and stability of mRNA have been identified and denoted post-transcriptional regulatory (PRE) elements. PRE sequences have been identified in the genome of human hepatitis B virus (the HPRE) and in the genome of the woodchuck hepatitis virus (WPRE). See, for example, Donello et al. (1998) *J. Virology* 72:5085-5092.

Expression of polypeptides (e.g., therapeutic antibodies, growth factors) in vitro is important for the pharmaceutical industry, and methods to maximize protein expression are needed.

SUMMARY

The present disclosure provides chimeric PRE sequences useful for generating expression constructs with improved stability and expression efficiency. In one embodiment, provided is a polynucleotide comprising (a) a first fragment consisting of the nucleic acid sequence of SEQ ID NO: 14 or a nucleic acid sequence having at least 95% sequence identity to SEQ ID NO: 14, and (b) a second fragment consisting of the nucleic acid sequence of SEQ ID NO: 3 or a nucleic acid sequence having at least 95% sequence identity to SEQ ID NO: 3.

In some aspects, the first fragment is not more than 20 nucleotides away from the second fragment. In some aspects, the first fragment is not more than 15, 10, 9, 8, 7, 6, 5, 4, 3, 2 or 1 nucleotide(s) away from the second fragment.

In some aspects, the polynucleotide further comprises a third fragment consisting of a gamma subelement of a post-transcriptional regulatory element (PRE). In some aspects, the gamma subelement has a nucleic acid sequence of SEQ ID NO: 7, 12, 16 or 20 or a nucleic acid sequence having at least 95% sequence identity to SEQ ID NO: 7, 12, 16 or 20. In some aspects, the gamma subelement has a nucleic acid sequence of SEQ ID NO: 7 or a nucleic acid sequence having at least 95% sequence identity to SEQ ID NO: 7. In some aspects, the gamma subelement has a nucleic acid sequence of SEQ ID NO: 16 or a nucleic acid sequence having at least 95% sequence identity to SEQ ID NO: 16.

In some aspects, the first fragment is between the third fragment and the second fragment. In some aspects, the third fragment is not more than 20 nucleotides away from the first fragment, or alternatively not more than 15, 10, 9, 8, 7, 6, 5, 4, 3, 2 or 1 nucleotide(s) away from the first fragment.

In some aspects, the polynucleotide comprises, sequentially, SEQ ID NOs: 7, 14 and 3. In some aspects, the polynucleotide comprises the nucleic acid sequence of SEQ ID NO: 26. In some aspects, the polynucleotide comprises the nucleic acid sequence of SEQ ID NO: 25.

Also provided, in one embodiment, is a polynucleotide comprising (a) a first fragment consisting of the nucleic acid sequence of SEQ ID NO: 7 or a nucleic acid sequence having at least 95% sequence identity to SEQ ID NO: 7, (b) a second fragment consisting of an alpha subelement of a post-transcriptional regulatory element (PRE), and (c) a third fragment consisting of the nucleic acid sequence of SEQ ID NO: 3 or a nucleic acid sequence having at least 95% sequence identity to SEQ ID NO: 3.

In some aspects, the alpha subelement has a nucleic acid sequence of SEQ ID NO: 2, 5, 9, 14 or 18, or a nucleic acid sequence having at least 95% sequence identity to SEQ ID NO: 2, 5, 9, 14 or 18. In some aspects, the alpha subelement has a nucleic acid sequence of SEQ ID NO: 2, or a nucleic acid sequence having at least 95% sequence identity to SEQ ID NO: 2. In some aspects, the second fragment is between the first fragment and the third fragment and each fragment is not more than 20 nucleotides away from a neighboring fragment or alternatively not more than 15, 10, 9, 8, 7, 6, 5, 4, 3, 2 or 1 nucleotide(s) away from the neighboring fragment.

In still another embodiment, the present disclosure provides a polynucleotide comprising (a) a first fragment consisting of the nucleic acid sequence of SEQ ID NO: 5, 9, or 18, or a nucleic acid sequence having at least 95% sequence identity to SEQ ID NO: 5, 9 or 18, and (b) a second fragment consisting of the nucleic acid sequence of SEQ ID NO: 3 or a nucleic acid sequence having at least 95% sequence identity to SEQ ID NO: 3. In some aspects, the polynucleotide further comprises (c) a third fragment consisting of a gamma subelement of a post-transcriptional regulatory element (PRE).

Also provided, in one embodiment, is a polynucleotide construct, comprising the polynucleotide of the present disclosure and a protein-coding sequence.

Also provided, in one embodiment, is a polynucleotide construct, comprising (a) a first fragment consisting of the nucleic acid sequence of SEQ ID NO: 14 or a nucleic acid sequence having at least 95% sequence identity to SEQ ID NO: 14, (b) a second fragment consisting of the nucleic acid sequence of SEQ ID NO: 3 or a nucleic acid sequence having at least 95% sequence identity to SEQ ID NO: 3 and (c) a protein-coding sequence.

Still, further provided in one embodiment is a polynucleotide construct, comprising (a) a first fragment consisting of the nucleic acid sequence of SEQ ID NO: 7 or a nucleic acid sequence having at least 95% sequence identity to SEQ ID NO: 7, (b) a second fragment consisting of an alpha subelement of a post-transcriptional regulatory element (PRE), (c) a third fragment consisting of the nucleic acid sequence of SEQ ID NO: 3 or a nucleic acid sequence having at least 95% sequence identity to SEQ ID NO: 3 and (d) (c) a protein-coding sequence.

Still, further provided in one embodiment is a polynucleotide construct, comprising (a) a first fragment consisting of the nucleic acid sequence of SEQ ID NO: 5, 9, or 18, or a nucleic acid sequence having at least 95% sequence identity to SEQ ID NO: 5, 9 or 18, (b) a second fragment consisting of the nucleic acid sequence of SEQ ID NO: 3 or a nucleic acid sequence having at least 95% sequence identity to SEQ ID NO: 3 and (c) a protein-coding sequence.

In one aspect of any of these embodiments, the protein-coding sequence is located between the first fragment and the second fragment. In one aspect, the construct further comprises a 3'-UTR. In one aspect, the 3'-UTR is located between the first fragment and the second fragment. In one aspect, the construct further comprises a poly(A) sequence.

Also provided, in one embodiment, is a cell comprising the polynucleotide construct of the present disclosure.

BRIEF DESCRIPTION OF THE DRAWINGS

FIG. 1 shows a multi-alignment of various α subelements. Figure discloses SEQ ID NOS 40-44, respectively, in order of appearance.

FIG. 2 shows a multi-alignment of various β subelements. Figure discloses SEQ ID NOS 3, 11, 15, 6 and 19, respectively, in order of appearance.

FIG. 3 shows a multi-alignment of various γ subelements. Figure discloses SEQ ID NOS 12, 20, 7 and 16, respectively, in order of appearance.

DETAILED DESCRIPTION

I. Definitions

Figure 4:
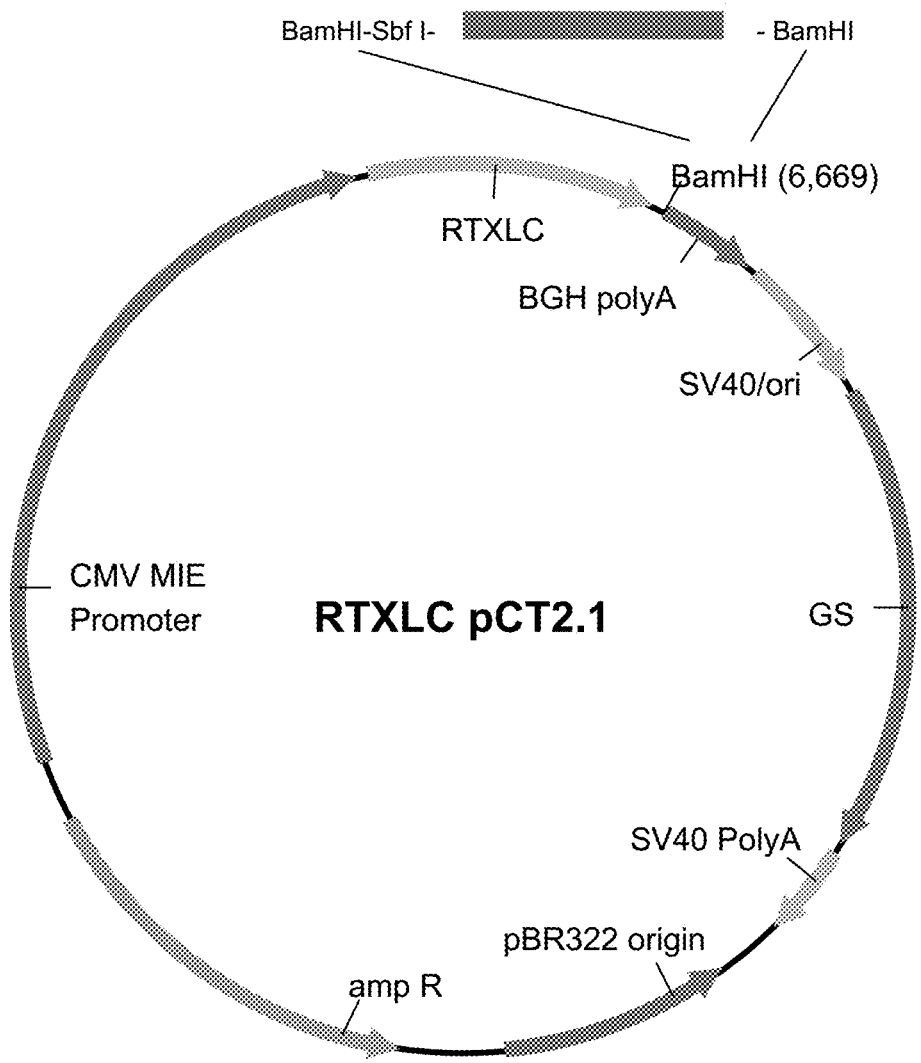
FIG. 4 shows a schematic drawing of the plasmid (pCT2.1) used for testing PRE elements. Different PREs were cloned into the BamHI site between the Rituximab light-chain coding sequences and the BGH polyadenylation signal.

All numerical designations, e.g., pH, temperature, time, concentration, and molecular weight, including ranges, are approximations which are varied (+) or (−) by increments of 0.1. It is to be understood, although not always explicitly stated that all numerical designations are preceded by the term "about". It also is to be understood, although not always explicitly stated, that the reagents described herein are merely exemplary and that equivalents of such are known in the art.

As used in the specification and claims, the singular form "a", "an" and "the" include plural references unless the context clearly dictates otherwise. For example, the term "a polynucleotide" includes a plurality of polynucleotides, including mixtures thereof.

The terms "polynucleotide" and "oligonucleotide" are used interchangeably and refer to a polymeric form of nucleotides of any length, either deoxyribonucleotides or ribonucleotides or analogs thereof. A polynucleotide can comprise modified nucleotides, such as methylated nucleotides and nucleotide analogs. If present, modifications to the nucleotide structure can be imparted before or after assembly of the polynucleotide. The sequence of nucleotides can be interrupted by non-nucleotide components. A polynucleotide can be further modified after polymerization, such as by conjugation with a labeling component. The term also refers to both double- and single-stranded molecules. Unless otherwise specified or required, any embodiment of this disclosure that is a polynucleotide encompasses both the double-stranded form and each of two complementary single-stranded forms known or predicted to make up the double-stranded form.

II. Chimeric Post-Transcriptional Regulatory Elements (PRE)

The Hepadnaviridae family of DNA viruses, such as the human hepatitis B virus (HBV), contain an RNA export element, termed the post-transcriptional regulatory element (PRE) that facilitates accumulation of surface antigen transcripts in the cytoplasm from the intronless hepadnavirus genome. A similar, more potent, tripartite PRE, is present in the woodchuck hepatitis virus (WHV), known as WHV PRE, or WPRE. Likewise, the human hepatitis B virus PRE is referred to as HPRE. WPRE increases transgene expression from a variety of viral vectors. In general, PRE sequences are useful for enhancing transient gene expression.

Some PRE sequences (e.g., HPRE) contain two individual and connected subelements, an α subelement (PREα) and a β subelement (PREβ; thus "bipartite"), while others (e.g., WPRE) contain an additional subelement, the γ subelement (PREγ; thus "tripartite"). Each of these subelements are fairly well conserved across species. See multiple sequence alignments in FIG. 1-3.

The mechanisms of how the PRE sequence influence gene expression is not entirely clear. Donello et al. explain that "the order of HPREα and HPREβ can be switched, suggesting that the subelements are modular [and thus t]he subelements most likely represent distinct binding sites for cellular RNA binding proteins" (Donello et al., J Virol. 1998 June; 72(6): 5085-5092 at 5085). Donello further discovered that "[t]he tripartite WPRE displays significantly stronger activity than the bipartite HBVPRE, demonstrating that the strength of the posttranscriptional effect is determined by the number of subelements in the RNA." Id. Therefore, the study suggested that the number of subelements, rather than the effectiveness of any individual subelement, was the primary factor to determine the strength of a PRE sequence.

Surprisingly and unexpectedly, however, experiments of the instant disclosure show that the strength of each individual played a significant role in determining the overall strength of the PRE sequence. Further, certain particular combinations of the subelements can be more effective than others. Accordingly, chimeric PREs with certain combinations of subelements from different PRE sequences are provided that have surprisingly high activity in increasing the stability and/or expression level of constructs that include these combinations.

In addition to WPRE and HPRE, other PRE sequences have been discovered from bat (BPRE), ground squirrel (GSPRE), arctic squirrel (ASPRE), duck (DPRE), chimpanzee (CPRE) and wooly monkey (WMPRE). The PRE sequences are typically highly conserved (see Table 1).

TABLE 1

Sequence identity with WPRE

| Source of PRE | Sequence Identity |
| --- | --- |
| Ground Squirrel | 84% |
| Arctic Squirrel | 82% |
| Bat | 74% |
| Human | 69% |
| Wooly Monkey | 69% |
| Chimpanzee | 67% |
| Duck | No significant similarity |

Table 2 below summarizes the relative activities of different PRE sequences, including native PRE sequences and chimeric PRE sequences.

TABLE 2

Relative activity of PRE sequences

| Construct | γ | α | β | Relative Activity (fold over control) |
| --- | --- | --- | --- | --- |
| 2.52 | WPRE | GSPRE | HPRE | 2.5 |
| 2.23 | GSPRE | GSPRE | HPRE | 2.16 |
| 2.5 | — | WPRE | HPRE | 2.12 |
| 2.4 | WPRE | GSPRE | GSPRE | 1.94 |
| 2.21 | — | BPRE | HPRE | 1.72 |
| 2.8 (GSPRE) | GSPRE | GSPRE | GSPRE | 1.63 |
| 2.0 (WPRE) | WPRE | WPRE | WPRE | 1.57 |
| 2.10 (ASPRE) | ASPRE | ASPRE | ASPRE | 1.52 |
| 2.7 | — | HPRE | WPRE | 1.27 |
| 2.9 (BPRE) | BPRE | BPRE | BPRE | 1.21 |
| 2.1 (Control) | — | — | — | 1 |

From Table 2, it can be seen that the α subelement from GSPRE, the β subelement from HPRE and the γ subelement from WPRE are the more active subelements of their types. Further, the following combinations exhibited superb activities: (1) the α subelement of GSPRE and the β subelement from HPRE, optionally with a γ subelement, (2) the γ subelement from WPRE and the β subelement from HPRE, and (3) the α subelement of WPRE, BPRE, or ASPRE and the β subelement from HPRE, optionally with a γ subelement.

In accordance with one embodiment of the present disclosure, therefore, provided is a chimeric PRE that includes a subelement of GSPRE (GSPREα) and the β subelement from HPRE (HPREβ), optionally with a γ subelement, each of which can be replaced with its biological equivalents.

A "biological equivalent" of a reference polynucleotide, as used herein, refers to a nucleic acid sequence that has a specific sequence identity to the reference polynucleotide, or is modified from the reference polynucleotide with limited nucleotide addition, deletion and/or substitution. In one embodiment, the specific sequence identity is at least 60%, 65%, 70%, 75%, 80%, 85%, 90%, 95%, 98% or alternatively 99%. In one embodiment, the biological equivalent is modified from the reference polynucleotide by no more than one, two, three, four, or alternatively five nucleotide additions, deletion, substitutions or their combinations.

The optional γ subelement of this combination can be any γ subelement from any PRE or their biological equivalents. In one aspect, the γ subelement is from WPRE, GSPRE, BPRE, or ASPRE. In one aspect, the γ subelement is from WPRE or GSPRE. In one aspect, the γ subelement is WPREγ.

In another embodiment, the chimeric PRE includes the γ subelement from WPRE (WPREγ), an α subelement from any PRE, and the β subelement from HPRE (HPREβ), each of which can be replaced with its biological equivalents. In some aspects, the α subelement is from GSPRE, HPRE, WPRE, BPRE or ASPRE, or is a biological equivalent of such an α subelement.

In another embodiment, the chimeric PRE includes the α subelement of WPRE, BPRE, or ASPRE and the β subelement from HPRE (HPREβ), optionally with a γ subelement. In one aspect, the α subelement is from WPRE. In one aspect, the α subelement is from BPRE. In one aspect, the α subelement is from ASPRE. In one aspect, the γ subelement is from WPRE. IN one aspect, the γ subelement is from GSPRE.

When the chimeric PRE only has an α subelement and a β subelement, in some aspects, the α subelement has the same orientation as and is downstream of the β subelement. In some aspects, the α subelement has the same orientation as and is upstream of the β subelement. In some aspects, the α subelement has the opposite orientation as compared to and is upstream of the β subelement. In some aspects, the α subelement has the opposite orientation as compared to and is downstream of the β subelement.

When the chimeric PRE has all three subelements, in some aspects, all three subelements have the same orientation. In one aspect, the order of the subelements, from upstream to downstream, is γ-α-β, γ-β-α, α-β-γ, β-α-γ, α-γ-β, or β-γ-α. In one aspect, in any of the above orders, just the α subelement has a reverse orientation. In one aspect, in any of the above orders, just the β subelement has a reverse orientation. In one aspect, in any of the above orders, just the γ subelement has a reverse orientation.

In any of the above embodiment, there can optionally be an additional α subelement, β subelement, and/or γ subelement, which can be placed adjacent to a subelement of its own type or separate by a subelement of different type.

In some aspects, a different transcription regulation element can be inserted between two adjacent subelements. For instance, a 5'-UTR or 3'-UTR can be inserted between an α subelement and β subelement, or between a γ subelement and an α subelement.

The distances between each subelements, or between a subelement and an adjacent UTR, in each of the above configurations can be adjusted. In one aspect, the distance between any adjacent subelement is not more than 50 nucleotides. In one aspect, the distance between any adjacent subelement is not more than 40, 30, 25, 20, 15, 10, 9, 8, 7, 6, 5, 4, 3, 2, or 1 nucleotides. In one aspect, the distance between any adjacent subelement is at least 1, 2, 3, 4, 5, or 10 nucleotides.

It is further contemplated that each of the subelments of the chimeric PRE of the present disclosure do not have to be adjacent to each other, but can be placed next to other elements of an expression construct. For instance, the α subelement and the β subelement can flank a gene of interest or a 3'-UTR. In one aspect, the α subelement is between the promoter and the gene of interest, and the β subelement is between the gene of interest and the 3'-UTR or after the 3'-UTR. In another aspect, the β subelement is between the promoter and the gene of interest, and the α subelement is between the gene of interest and the 3'-UTR or after the 3'-UTR. In one aspect, both the α and β subelements are between the promoter and the gene of interest or between the gene of interest and the 3'-UTR. When a γ subelement is used, it can be placed at any of the above locations, which can be before the promoter, between the promoter and the gene of interest, between the gene of interest and the 3'-UTR, or after the 3'-UTR.

The sequences of HPRE, WPRE, GSPRE, BPRE, and ASPRE as well as their individual subelements with modified versions are provided in Table 3 below. In general, nucleotides of the α subelements are underlined, of the β subelements are bold, and of the γ subelements are italic.

TABLE 3

Sequences of the native HPRE, WPRE, GSPRE, BPRE, and ASPRE and the individual subelements, native or modified

| HPRE (SEQ ID NO: 1) | 1 AAACAGGCCT ATTGATTGGA AAGTTTGTCA ACGAATTGTG GGTCTTTTGG |
| --- | --- |
| | 51 GGTTTGCTGC CCCTTTTACG CAATGTGGAT ATCCTGCTTT AATGCCTTTA |
| | 101 TATGCATGTA TACAAGCAAA ACAGGCTTTT ACTTTCTCGC CAACTTACAA |
| | 151 GGCCTTTCTC AGTAAACAGT ATATGACCCT TTACCCCGTT GCTCGGCAAC |
| | 201 GGCCTGGTCT GTGCCAAGTG TTTGCTGACG CAACCCCCAC TGGTTGGGGC |
| | 251 TTGGCCATAG GCCATCAGCG CATGCGTGGA ACCTTTGTGT CTCCTCTGCC |
| | 301 GATCCATACT GCGGAACTCC TAGCCGCTTG TTTTGCTCGC AGCAGGTCTG |
| | 351 GAGCAAACCT CATCGGGACC GACAATTCTG TCGTACTCTC CCGCAAGTAT |
| | 401 ACATCGTTTC CATGGCTGCT AGGCTGTGCT GCCAACTGGT ACCTGCGCGG |
| | 451 GACGTCCTTT GTTTACGTCC CGTCGGCGCT GAATCCCGCG GACGACCCCT |
| | 501 CCCGGGGCCG CTTGGGGCTC TACCGCCCGC TTCTCCGTCT GCCGTACCGT |
| | 551 CCGACCACGG GGCGCACCTC TCTTTACGCG GACTCCCCGT CTGTGCCTTC |
| | 601 TCATCTGCCG GACCGTGTGC ACTTCGCTTC ACCTCTGCAC GTCGCATGGA |
| | 651 GACCACCGTG AACGCCCACC GGAACCTGCC CAAGGTCTTG CATAAGAGGA |
| | 701 CTCTTGGACT TTCAGCAATG TC |

| HPREα (SEQ ID NO: 2) | 1 GTTGCTCGGC AACGGCCTGG TCTGTGCCAA GTGTTTGCTG ACGCAACCCC |
| --- | --- |
| | 51 CACTGGTTGG GGCTTGGCCA TAGGCCATCA GCGCATGCGT GGAACCTTTG |
| | 101 TGTCTCCTCT GCCGATCCAT ACTGCGGAAC TCCTAGCCGC TTGTTTTGCT |
| | 151 CGCAGCAGGT CTGGAGCAAA CCTCATCGGG ACCGACAATT CTGTCGTACT |
| | 201 CTCCCGCAAG TATACATCGT TTCCATGGCT GCTAGGCTGT GCTGCCAACT |
| | 251 GGTACCTGCG C |

| HPREβ (SEQ ID NO: 3) | 1 GGGACGTCCT TTGTTTACGT CCCGTCGGCG CTGAATCCCG CGGACGACCC |
| --- | --- |
| | 51 CTCCCGGGGC CGCTTGGGGC TCTACCGCCC GCTTCTCCGT CTGCCGTACC |
| | 101 GTCCGACCAC GGGGCGCACC TCTCTTTACG CGGACTCCCC GTCTGTGCCT |
| | 151 TCTCATCTGC CGGACCGTGT GC |

| WPRE (SEQ ID NO: 4) | 1 *GATCCAATCA ACCTCTGGAT TACAAAATTT GTGAAAGATT GACTGGTATT* |
| --- | --- |
| | 51 *CTTAACTATG TTGCTCCTTT TACGCTATGT GGATACGCTG CTTTAATGCC* |
| | 101 *TTTGTATCAT GCTATTGCTT CCCGTATGGC TTTCATTTTC TCCTCCTTGT* |
| | 151 *ATAAATCCTG GTTGCTGTCT CTTTATGAGG AGTTGTGGCC* CGTTGTCAGG |
| | 201 CAACGTGGCG TGGTGTGCAC TGTGTTTGCT GACGCAACCC CCACTGGTTG |
| | 251 GGGCATTGCC ACCACCTGTC AGCTCCTTTC CGGGACTTTC GCTTTCCCCC |
| | 301 TCCCTATTGC CACGGCGGAA CTCATCGCCG CCTGCCTTGC CCGCTGCTGG |
| | 351 ACAGGGGCTC GGCTGTTGGG CACTGACAAT TCCGTGGTGT TGTCGGGGAA |
| | 401 GCTGACGTCC TTTCCATGGC TGCTCGCCTG TGTTGCCACC TGGATTCTGC |
| | 451 GCGGGACGTC CTTCTGCTAC GTCCCTTCGG CCCTCAATCC AGCGGACCTT |
| | 501 CCTTCCCGCG GCCTGCTGCC GGCTCTGCGG CCTCTTCCGC GTCTTCGCCT |
| | 551 TCGCCCTCAG ACGAGTCGGA TCTCCCTTTG GGCCGCCTCC CCGCCTGGGA |
| | 601 TC |

| WPREα (SEQ ID NO: 5) | 1 GTTGTCAGGC AACGTGGCGT GGTGTGCACT GTGTTTGCTG ACGCAACCCC |
| --- | --- |
| | 51 CACTGGTTGG GGCATTGCCA CCACCTGTCA GCTCCTTTCC GGGACTTTCG |
| | 101 CTTTCCCCCT CCCTATTGCC ACGGCGGAAC TCATCGCCGC CTGCCTTGCC |
| | 151 CGCTGCTGGA CAGGGGCTCG GCTGTTGGGC ACTGACAATT CCGTGGTGTT |
| | 201 GTCGGGGAAG CTGACGTCCT TTCCATGGCT GCTCGCCTGT GTTGCCACCT |
| | 251 GGATTCTGCG C |

| WPREβ (SEQ ID NO: 6) | 1 GGGACGTCCT TCTGCTACGT CCCTTCGGCC CTCAATCCAG CGGACCTTCC |
| --- | --- |
| | 51 TTCCCGCGGC CTGCTGCCGG CTCTGCGGCC TCTTCCGCGT CTTCGCCTTC |
| | 101 GCCCTCAGAC GAGTCGGATC TCCCTTTGGG CCGCCTCCCC GCCTGGGATC |

| WPREγ (SEQ ID NO: 7) | 1 AATCAACCTC TGGATTACAA AATTTGTGAA AGATTGACTG GTATTCTTAA |
| --- | --- |
| | 51 CTATGTTGCT CCTTTTACGC TATGTGGATA CGCTGCTTTA ATGCCTTTGT |
| | 101 ATCATGCTAT TGCTTCCCGT ATGGCTTTCA TTTTCTCCTC CTTGTATAAA |
| | 151 TCCTGGTTGC TGTCTCTTTA TGAGGAGTTG TGGCCC |

| BPRE (SEQ ID NO: 8) | 1 *AACAAGCCTT TGGATTGGAA AATCCTTCAG CGCATTACGG GTCTCCTGGG* |
| --- | --- |
| | 51 *GTTTCTTGCA CCCTTCACGA CCTGTGGCTA TCCAGCCCTA ATGCCTTTGT* |
| | 101 *ACCATGCCAT TACCCGGCGC CAGGCCTTAA AAATTTCCTG GCCCTTTAAG* |
| | 151 *ACCTTTCTTT ACAGCCTGTA CAAGCAACCT TTGCCC*GTTA TCAGGCAGAA |
| | 201 GCGGGCAATC TGCCAGGTGT TTGCTGACGC AACCCCCACT GGTTGGGGCC |
| | 251 TGGTTAATCA TTCCTCCGCA TGGTTGCGCA GGGGACGGTT TCCCCGCCCC |
| | 301 TTGCCTATCC ATTGCGCGGA ACTTATTGCC GCCTGCCTTG CTCGCCGCTG |
| | 351 GACGGGAGCT CGGGTTATTG GAACTGACAA TTCCATTGTG GCTTCGGGAA |
| | 401 AGCGGACATC TTTCCCATGG CTGCTCGGCT GCGTTGCCAA CTGGATGCTT |
| | 451 CGGGGAACGT CGTTCTGCTT CGTCCCCTCT GCATTGAATC CGGCGGACGC |
| | 501 CCCGTCGCGC GGACTGCTCG GCATTCCCGT CGCGCCGCCG CCTCTCCCGT |
| | 551 TCCGACCTTC TACGGGCCGC ACGTCACTCT TCGCCGTCTC CCCATCTG |

TABLE 3 -continued

Sequences of the native HPRE, WPRE, GSPRE, BPRE, and ASPRE and the individual subelements, native or modified

```
BPREα (SEQ ID      1 GTTATCAGGC AGAAGCGGGC AATCTGCCAG GTGTTTGCTG ACGCAACCCC
NO: 9)            51 CACTGGTTGG GGCCTGGTTA ATCATTCCTC CGCATGGTTG CGCAGGGGAC
                 101 GGTTTCCCCG CCCCTTGCCT ATCCATTGCG CGGAACTTAT TGCCGCCTGC
                 151 CTTGCTCGCC GCTGGACGGG AGCTCGGGTT ATTGAACTGA CAATTCCAT
                 201 TGTGGCTTCG GGAAAGCGGA CATCTTTCCC ATGGCTGCTC GGCTGCGTTG
                 251 CCAACTGGAT GCTTCGGGC

BPREα             1 GTTATCAGGC AGAAGCGGGC AATCTGCCAG GTGTTTGCTG ACGGAACCCC
modified (SEQ    51 CACTGGTTGG GGCCTGGTTA ATCATTCCTC CGCATGGTTC CGCAGGGGAC
ID NO: 10)      101 GGTTTCCCCG CCCCTTGCCT ATCCATTGCG CGGAACTTAT TGCCGCCTGC
                 151 CTTGCTCGCC GCTGGACGGG AGCTCGGGTT ATTGAACTGA CAATTCCAT
                 201 TGTGGCTTCG GGAAAGCGGA CATCTTTCCC ATGGCTGCTC GGCTGCGTTG
                 251 CCAACTGGAT GCTTCGGGC BPREβ (SEQ ID     1 GAACGTCGTT CTGCTTCGTC CCCTCTGCAT TGAATCCGGC GGACGCCCCG
NO: 11)          51 TCGCGCGGAC TGCTCGGCAT TCCCGTCGCG CCGCCGCCTC TCCCGTTCCG
                101 ACCTTCTACG GGCCGCACGT CACTCTTCGC CGTCTCCCCA TCTG BPREγ (SEQ ID     1 AACAAGCCTT TGGATTGGAA AATCCTTCAG CGCATTACGG GTCTCCTGGG
NO: 12)          51 GTTTCTTGCA CCCTTCACGA CCTGTGGCTA TCCAGCCCTA ATGCCTTTGT
                101 ACCATGCCAT TACCCGGCGC CAGGCCTTAA AAATTTCCTG GCCCTTTAAG
                151 ACCTTTCTTT ACAGCCTGTA CAAGCAACCT TTGCCC GSPRE (SEQ ID     1 AATCAACCCT TAGATTATAA AATATGTGAA AGGTTGACGG GCATTCTTAA
NO: 13)          51 TTATGTTGCT CCTTTTACCA AATGTGGTTA TGCTGCTTTA CTGCCTTTAT
                101 ATCAAGCTAT TGCTTCTCAT ACTGCTTTTG TTTTCTCCTC CTTATATAAA
                151 AACTGGTTAC TGTCACTTTA TGGTGAGTTG TGGCCCGTTG CCAGACAACG
                201 TGGTGTGGTG TGCTCTGTGT TTGCTGACGC AACTCCCACT GGTTGGGGCA
                251 TTTGCACCAC CTGTCAACTC ATTTCCGGTA CTTTCGGTTT CTCACTTCCG
                301 ATTGCTACCG CGGAGCTTAT AGCCGCCTGC CTTGCTCGCT GCTGGACAGG
                351 AGCTCGGTTG TTGGGCACTG ATAACTCCGT GGTCCTCTCC GGTAAGCTAA
                401 CTTCGTTTCC ATGGCTGCTC GCCTGTGTTG CCAACTGGAT TCTTCGCGGG
                451 ACGTCCTTCT GTTACGTCCC CTCCGCGGAC AACCCAGCGG ACCTTCCGTC
                501 TCGGGGACTT CTGCCGGCTC TCCGTCCTCT GCCGCTTCTG CGTTTTCGTC
                551 CGGTCACCAA GCGGATATCC CTGTGGGCCG CCTCCCCGCC TG GSPREα (SEQ       1 GTTGCCAGAC AACGTGGTGT GGTGTGCTCT GTGTTTGCTG ACGCAACTCC
ID NO: 14)       51 CACTGGTTGG GGCATTTGCA CCACCTGTCA ACTCATTTCC GGTACTTTCG
                101 GTTTCTCACT TCCGATTGCT ACCGCGGAGC TTATAGCCGC CTGCCTTGCT
                151 CGCTGCTGGA CAGGAGCTCG GTTGTTGGGC ACTGATAACT CCGTGGTCCT
                201 CTCCGGTAAG CTAACTTCGT TTCCATGGCT GCTCGCCTGT GTTGCCAACT
                251 GGATTCTTCG C GSPREβ (SEQ       1 GGGACGTCCT TCTGTTACGT CCCCTCCGCG GACAACCCAG CGGACCTTCC
ID NO: 15)       51 GTCTCGGGGA CTTCTGCCGG CTCTCCGTCC TCTGCCGCTT CTGCGTTTTC
                101 GTCCGGTCAC CAAGCGGATA TCCCTGTGGG CCGCCTCCCC GCCTG GSPREγ (SEQ       1 AATCAACCCT TAGATTATAA AATATGTGAA AGGTTGACGG GCATTCTTAA
ID NO: 16)       51 TTATGTTGCT CCTTTTACCA AATGTGGTTA TGCTGCTTTA CTGCCTTTAT
                101 ATCAAGCTAT TGCTTCTCAT ACTGCTTTTG TTTTCTCCTC CTTATATAAA
                151 AACTGGTTAC TGTCACTTTA TGGTGAGTTG TGGCCC ASPRE (SEQ ID     1 AACCTTTAGA TTATAAAATC TGTGAAAGGT TAACAGGCAT TCTGAATTAT
NO: 17)          51 GTTGCTCCTT TTACTAAATG TGGTTATGCT GCTCTCCTTC CTTTGTATCA
                101 AGCTACTTCG CGTACGGCAT TTGTGTTTTC TTCTCTCTAC CACAGCTGGT
                151 TGCTGTCCCT TTATGCTGAG TTGTGGCCTG TTGCCAGGCA ACGTGGCGTG
                201 GTGTGCTCTG TGTCTGACGC AACCCCCACT GGTTGGGGCA TTTGCACCAC
                251 CTATCAACTC ATTTCCCCGA CGGGCGCTTT TGCCCTGCCG ATCGCCACCG
                301 CGGACGTCAT CGCCGCCTGC CTTGCTCGCT GCTGGACAGG AGCTCGGCTG
                351 TTGGGCACTG ACAACTCCGT GGTTCTTTCG GGCAAACTGA CTTCCTATCC
                401 ATGGCTGCTC GCCTGTGTTG CCAACTGGAT TCTTCGCGGG ACGTCGTTCT
                451 GCTACGTCCC TTCGGCAGCG AATCCGGCGG ACCTGCCGTC TCGAGGCCTT
                501 CTGCCGGCTC TGCATCCCGT GCCGACTCTC CGCTTCCGTC CGCAGCTGAG
                551 TCGCATCTCC CTTTGGGCCG CCTCCCCGCC TG ASPREα (SEQ       1 GTTGCCAGGC AACGTGGCGT GGTGTGCTCT GTGTCTGACG CAACCCCCAC
ID NO: 18)       51 TGGTTGGGGC ATTTGCACCA CCTATCAACT CATTTCCCCG ACGGGCGCTT
                101 TTGCCCTGCC GATCGCCACC GCGGACGTCA TCGCCGCCTG CCTTGCTCGC
                151 TGCTGGACAG GAGCTCGGCT GTTGGGCACT GACAACTCCG TGGTTCTTTC
                201 GGGCAAACTG ACTTCCTATC CATGGCTGCT CGCCTGTGTT GCCAACTGGA
                251 TTCTTCGC ASPREβ (SEQ       1 GGGACGTCGT TCTGCTACGT CCCTTCGGCA GCGAATCCGG CGGACCTGCC
ID NO: 19)       51 GTCTCGAGGC CTTCTGCCGG CTCTGCATCC CGTGCCGACT CTCCGCTTCC
                101 GTCCGCAGCT GAGTCGCATC TCCCTTTGGG CCGCCTCCCC GCCTG
```

TABLE 3 -continued

Sequences of the native HPRE, WPRE, GSPRE, BPRE, and ASPRE and the individual subelements, native or modified

| ASPREγ (SEQ ID NO: 20) | | |
|---|---|---|
| | 1 | AACCTTTAGA TTATAAAATC TGTGAAAGGT TAACAGGCAT TCTGAATTAT |
| | 51 | GTTGCTCCTT TTACTAAATG TGGTTATGCT GCTCTCCTTC CTTTGTATCA |
| | 101 | AGCTACTTCG CGTACGGCAT TTGTGTTTTC TTCTCTCTAC CACAGCTGGT |
| | 151 | TGCTGTCCCT TTATGCTGAG TTGTGGCCT |

SEQ ID NOs of the sequences in the above table are summarized in Table 4 below.

TABLE 4

Summary of SEQ ID NOs

| PRE | all | γ | α | β |
|---|---|---|---|---|
| HPRE | 1 | — | 2 | 3 |
| WPRE | 4 | 7 | 5 | 6 |
| BPRE | 8 | 12 | 9 | 11 |
| GSPRE | 13 | 16 | 14 | 15 |
| ASPRE | 17 | 20 | 18 | 19 |

The sequences of some tested chimeric PRE sequences are provided in Table 5 below.

TABLE 5

Sequences of chimeric PREs

| WPREγ/GSPREα/ GSPREβ (PCT 2.4) (SEQ ID NO: 21) | | |
|---|---|---|
| | 1 | AATCAACCTC TGGATTACAA AATTTGTGAA AGATTGACTG GTATTCTTAA |
| | 51 | CTATGTTGCT CCTTTTACGC TATGTGGATA CGCTGCTTTA ATGCCTTTGT |
| | 101 | ATCATGCTAT TGCTTCCCGT ATGGCTTTCA TTTTCTCCTC CTTGTATAAA |
| | 151 | TCCTGGTTGC TGTCTCTTTA TGAGGAGTTG TGGCCCGTTG CCAGACAACG |
| | 201 | TGGTGTGGTG TGCTCTGTGT TTGCTGACGC AACTCCCACT GGTTGGGGCA |
| | 251 | TTTGCACCAC CTGTCAACTC ATTTCCGGTA CTTTCGGTTT CTCACTTCCG |
| | 301 | ATTGCTACCG CGGAGCTTAT AGCCGCCTGC CTTGCTCGCT GCTGGACAGG |
| | 351 | AGCTCGGTTG TTGGGCACTG ATAACTCCGT GGTCCTCTCC GGTAAGCTAA |
| | 401 | CTTCGTTTCC ATGGCTGCTC GCCTGTGTTG CCAACTGGAT TCTTCGCGGG |
| | 451 | ACGTCCTTCT GTTACGTCCC CTCCGCGGAC AACCCAGCGG ACCTTCCGTC |
| | 501 | TCGGGGACTT CTGCCGGCTC TCCGTCCTCT GCCGCTTCTG CGTTTTCGTC |
| | 551 | CGGTCACCAA GCGGATATCC CTGTGGGCCG CCTCCCCGCC TG |
| HPREα/WPREβ (PCT 2.7) (SEQ ID NO: 22) | | |
| | 1 | GTTGCTCGGC AACGGCCTGG TCTGTGCCAA GTGTTTGCTG ACGCAACCCC |
| | 51 | CACTGGTTGG GGCTTGGCCA TAGGCCATCA GCGCATGCGT GGAACCTTTG |
| | 101 | TGTCTCCTCT GCCGATCCAT ACTGCGGAAC TCCTAGCCGC TTGTTTTGCT |
| | 151 | CGCAGCAGGT CTGGAGCAAA CCTCATCGGG ACCGACAATT CTGTCGTACT |
| | 201 | CTCCCGCAAG TATACATCGT TTCCATGGCT GCTAGGCTGT GCTGCCAACT |
| | 251 | GGTACCTGCG CGGGACGTCC TTCTGCTACG TCCCTTCGGC CCTCAATCCA |
| | 301 | GCGGACCTTC CTTCCCGCGG CCTGCTGCCG GCTCTGCGGC CTCTTCCGCG |
| | 351 | TCTTCGCCTT CGCCCTCAGA CGAGTCGGAT CTCCCTTTGG GCCGCCTCCC |
| | 401 | CGCCTGGGAT C |
| WPREα/HPREβ short (PCT 2.5) (SEQ ID NO: 39) | | |
| | 1 | GTTGTCAGGC AACGTGGCGT GGTGTGCACT GTGTTTGCTG ACGCAACCCC |
| | 51 | CACTGGTTGG GGCATTGCCA CCACCTGTCA GCTCCTTTCC GGGACTTTCG |
| | 101 | CTTTCCCCCT CCCTATTGCC ACGGCGGAAC TCATCGCCGC CTGCCTTGCC |
| | 151 | CGCTGCTGGA CAGGGGCTCG GCTGTTGGGC ACTGACAATT CCGTGGTGTT |
| | 201 | GTCGGGGAAG CTGACGTCCT TTCCATGGCT GCTCGCCTGT GTTGCCACCT |
| | 251 | GGATTCTGCG CGGGACGTCC TTTGTTTACG TCCCGTCGGC GCTGAATCCC |
| | 301 | GCGGACGACC CCTCCCGGGG CCGCTTGGGG CTCTACCGCC CGCTTCTCCG |
| | 351 | TCTGCCGTAC CGTCCGACCA CGGGGCGCAC TCTCTTTAC GCGGACTCCC |
| | 401 | CGTCTGTGCC TTTCTCATCTG CCGGACCGTG TGC |
| BPREα/HPREβ (PCT 2.21) (SEQ ID NO: 23) | | |
| | 1 | GTTATCAGGC AGAAGCGGGC AATCTGCCAG GTGTTTGCTG ACGCAACCCC |
| | 51 | CACTGGTTGG GGCCTGGTTA ATCATTCCTC CGCATGGTTG CGCAGGGGAC |
| | 101 | GGTTTCCCCG CCCCTTGCCT ATCCATTGCG CGGAACTTAT TGCCGCCTGC |
| | 151 | CTTGCTCGCC GCTGGACGGG AGCTCGGGTT ATTGGAACTG ACAATTCCAT |
| | 201 | TGTGGCTTCG GGAAAGCGGA CATCTTTCCC ATGGCTGCTC GGCTGCGTTG |
| | 251 | CCAACTGGAT GCTTCGGGCG GGACGTCCTT TGTTTACGTC CCGTCGGCGC |
| | 301 | TGAATCCCGC GGACGACCCC TCCCGGGGCC GCTTGGGGCT CTACCGCCCG |
| | 351 | CTTCTCCGTC TGCCGTACCG TCCGACCACG GGGCGCACCT CTCTTTACGC |
| | 401 | GGACTCCCCG TCTGTGCCTT CTCATCTGCC GGACCGTGTG CACTTCGCTT |
| | 451 | CACCTCTGCA CGTCGCATGG AGACCACCGT GAACGCCCAC CGGAACCTGC |
| | 501 | CCAAGGTCTT GCATAAGAGG ACTCTTGGAC TTTCAGCAAT GTC |
| BPREα mod/HPREβ (PCT 2.22) (SEQ ID NO: 24) | | |
| | 1 | GTTATCAGGC AGAAGCGGGC AATCTGCCAG GTGTTTGCTG ACGGAACCCC |
| | 51 | CACTGGTTGG GGCCTGGTTA ATCATTCCTC CGCATGGTTC CGCAGGGGAC |
| | 101 | GGTTTCCCCG CCCCTTGCCT ATCCATTGCG CGGAACTTAT TGCCGCCTGC |
| | 151 | CTTGCTCGCC GCTGGACGGG AGCTCGGGTT ATTGGAACTG ACAATTCCAT |
| | 201 | TGTGGCTTCG GGAAAGCGGA CATCTTTCCC ATGGCTGCTC GGCTGCGTTG |
| | 251 | CCAACTGGAT GCTTCGGGCG GGACGTCCTT TGTTTACGTC CCGTCGGCGC |

TABLE 5 -continued

Sequences of chimeric PREs

|  |  |
|---|---|
|  | 301 TGAATCCCGC GGACGACCCC TCCCGGGGCC GCTTGGGGCT CTACCGCCCG<br>351 CTTCTCCGTC TGCCGTACCG TCCGACCACG GGGCGCACCT CTCTTTACGC<br>401 GGACTCCCCG TCTGTGCCTT CTCATCTGCC GGACCGTGTG CACTTCGCTT<br>451 CACCTCTGCA CGTCGCATGG AGACCACCGT GAACGCCCAC CGGAACCTGC<br>501 CCAAGGTCTT GCATAAGAGG ACTCTTGGAC TTTCAGCAAT GTC |
| GSPREγ/GSPREα/<br>HPREβ (PCT<br>2.23) (SEQ ID<br>NO: 25) | 1 AATCAACCCT TAGATTATAA AATATGTGAA AGGTTGACGG GCATTCTTAA<br>51 TTATGTTGCT CCTTTTACCA AATGTGGTTA TGCTGCTTTA CTGCCTTTAT<br>101 ATCAAGCTAT TGCTTCTCAT ACTGCTTTTG TTTTCTCCTC CTTATATAAA<br>151 AACTGGTTAC TGTCACTTTA TGGTGAGTTG TGGCCCGTTG CCAGACAACG<br>201 TGGTGTGGTG TGCTCTGTGT TTGCTGACGC AACTCCCACT GGTTGGGGCA<br>251 TTTGCACCAC CTGTCAACTC ATTTCCGGTA CTTTCGGTTT CTCACTTCCG<br>301 ATTGCTACCG CGGAGCTTAT AGCCGCCTGC CTTGCTGCT GCTGGACAGG<br>351 AGCTCGGTTG TTGGGCACTG ATAACTCCGT GGTCCTCTCC GGTAAGCTAA<br>401 CTTCGTTTCC ATGGCTGCTC GCCTGTGTTG CCAACTGGAT TCTTCGCCGG<br>451 GACGTCCTTT GTTTACGTCC CGTCGGCGCT GAATCCCGCG GACGACCCCT<br>501 CCCGGGGCCG CTTGGGGCTC TACCGCCCGC TTCTCCGTCT GCCGTACCGT<br>551 CCGACCACGG GGCGCACCTC TCTTTACGCG GACTCCCCGT CTGTGCCTTC<br>601 TCATCTGCCG GACCGTGTGC ACTTCGCTTC ACCTCTGCAC GTCGCATGGA<br>651 GACCACCGTG AACGCCCACC GGAACCTGCC CAAGGTCTTG CATAAGAGGA<br>701 CTCTTGGACT TTCAGCAATG TC |
| WPREγ/GSPREα/<br>HPREβ (PCT<br>2.52) (SEQ ID<br>NO: 26) | 1 GATCCAATCA ACCTCTGGAT TACAAATTT GTGAAAGATT GACTGGTATT<br>51 CTTAACTATG TTGCTCCTTT TACGCTATGT GGATACGCTG CTTTAATGCC<br>101 TTTGTATCAT GCTATTGCTT CCCGTATGGC TTTCATTTTC TCCTCCTTGT<br>151 ATAAATCCTG GTTGCTGTCT CTTTATGAGG AGTTGTGGCC CGTTGCCAGA<br>201 CAACGTGGTG TGGTGTGCTC TGTGTTTGCT GACGCAACTC CCACTGGTTG<br>251 GGGCATTTGC ACCACCTGTC AACTCATTTC CGGTACTTTC GGTTTCTCAC<br>301 TTCCGATTGC TACCGCGGAG CTTATAGCCG CCTGCCTTGC TCGCTGCTGG<br>351 ACAGGAGCTC GGTTGTTGGG CACTGATAAC TCCGTGGTCC TCTCCGGTAA<br>401 GCTAACTTCG TTTCCATGGC TGCTCGCCTG TGTTGCCAAC TGGATTCTTC<br>451 GCGGGACGTC CTTTGTTTAC GTCCCGTCGG CGCTGAATCC CGCGGACGAC<br>501 CCCTCCCGGG GCCGCTTGGG GCTCTACCGC CCGCTTCTCC GTCTGCCGTA<br>551 CCGTCCGACC ACGGGGCGCA CCTCTCTTTA CGCGGACTCC CCGTCTGTGC<br>601 CTTCTCATCT GCCGGACCGT GTGCACTTCG CTTCACCTCT GCACGTCGCA<br>651 TGGAGACCAC CGTGAACGCC CACCGGAACC TGCCCAAGGT CTTGCATAAG<br>701 AGGACTCTTG GACTTTCAGC AATGTC |

Table 6 below shows the sequences of some additional PRE sequences and their subelements, which can be used for generating chimeric PREs of the present disclosure.

TABLE 6

Sequences of additional native PREs

|  |  |
|---|---|
| Duck PRE<br>(DPRE) (SEQ<br>ID NO: 27) | 1 AAGATTTGTT GGGCATTTGA ACTTTGTGTT ACCATTTACT AAAGGTAACA<br>51 TTGAAATGTT AAAACCAATG TATGCTGCTA TTACTAACAA AGTTAACTTT<br>101 AGCTTCTCTT CAGCTTATAG GACTTTATTG TACAAATTAA CTATGGGTGT<br>151 TTGTAAATTA GCCATTCGAC CAAAGTCCTC TGTACCTTTG CCACGTGTAG<br>201 CCACAGATGC TACTCCAACA CATGGCGCAA TATCCCATAT CACCGGCGGG<br>251 AGCGCAGTGT TTGCTTTTTC AAAGGTCAGG GATATACATA TACAGGAATT<br>301 GCTGATGGTA TGTTTAGCTA AGATAATGAT TAAACCCAGA TGTATACTCT<br>351 CCGATTCTAC TTTTGTTTGC CACAAACGTT ATCAGACGTT ACCATGGCAT<br>401 TTTGCTATGT TGGCCAAACA ACTGCTATCT CCTATACAGT TGTACTTTGT<br>451 TCCAAGTAAA TACAATCCTG CTGACGGCCC ATCCAGGCAC AGACCGCCTG<br>501 ATTGGACGGC TCTTACATAC ACCCCTCTCT CGAAAGCAAT ATATATTCCA<br>551 CATAGGCTAT G |
| DPREα (SEQ ID<br>NO: 28) | 1 GTCCTCTGTA CCTTTGCCAC GTGTAGCCAC AGATGCTACT CCAACACATG<br>51 GCGCAATATC CCATATCACC GGCGGGAGCG CAGTGTTTGC TTTTTCAAAG<br>101 GTCAGGGATA TACATATACA GGAATTGCTG ATGGTATGTT TAGCTAAGAT<br>151 AATGATTAAA CCCAGATGTA TACTCTCCGA TTCTACTTTT GTTTGCCACA<br>201 AACGTTATCA GACGTTACCA TGGCATTTTG CTATGTTGGC CAAACAACTG<br>251 CTATCT |
| DPREβ (SEQ ID<br>NO: 29) | 1 CCTATACAGT TGTACTTTGT TCCAAGTAAA TACAATCCTG CTGACGGCCC<br>51 ATCCAGGCAC AGACCGCCTG ATTGGACGGC TCTTACATAC ACCCCTCTCT<br>101 CGAAAGCAAT ATATATTCCA CATAGGCTAT G |
| DPREγ (SEQ ID<br>NO: 30) | 1 AAGATTTGTT GGGCATTTGA ACTTTGTGTT ACCATTTACT AAAGGTAACA<br>51 TTGAAATGTT AAAACCAATG TATGCTGCTA TTACTAACAA AGTTAACTTT<br>101 AGCTTCTCTT CAGCTTATAG GACTTTATTG TACAAATTAA CTATGGGTGT<br>151 TTGTAAATTA GCCATTCGAC CAAA |

TABLE 6 -continued

Sequences of additional native PREs

```
Chimpanzee      1 AACAGACCTA TAGATTGGAA AGTATGTCAA AGAATTGTGG GTCTTTTGGG
(CPRE) (SEQ    51 ATTTGCTGCC CCTTTTACGC AATGTGGTTA TCCTGCGTTA ATGCCATTGT
ID NO: 31)    101 ATGCATGTAT ACAAGCAAAA CAGGCTTTCA CTTTCTCGCC AACTTATAAG
              151 GCCTTTCTAA GTCAACAATA TTCGACCCTT TACCCCGTTG CCCGGCAACG
              201 GTCCGGTCTG TGCCAAGTGT TTGCTGACGC AACCCCCACT GGCTGGGGCT
              251 TGGTCATGGG CCATCAGCGC ATGCGTGGAA CCTTTGTGGC TCCTCTGCCG
              301 ATCCATACTG CGGAACTCCT AGCAGCTTGT TTTGCTCGCA GCCGGTCTGG
              351 AGCAAAACTT ATCGGAACTG ACAATTCTGT CGTCCTCTCT CGGAAATATA
              401 CATCTTTTCC ATGGCTGCTA GGTTGTGCTG CCAACTGGAT ACTTCGCGGG
              451 ACGTCCTTTG TTTACGTCCC GTCGGCGCTG AATCCTGCGG ACGACCCTTC
              501 TCGGGGCCGC TTAGGGCTCT ACCGCCCTCT CATCCGTCTG CTCTTCCAAC
              551 CGACTACGGG GCGCACCTCT CTTTACGCGG TCTCCCGCTG TGCCTTCTCA
              601 TCTGCCGGTC CGTGTGCACT TCGCTTCACC TCTGCACGTT GCATGGAGAC
              651 CACCGTGAAC GCCCCACGGA ACCTGCCAAA AGTCTTGCAT AAGAGGACTC
              701 TTGGACTTTC AGCAATGTC CPREα (SEQ ID   1 CGTTGCCCGG CAACGGTCCG GTCTGTGCCA AGTGTTTGCT GACGCAACCC
NO: 32)        51 CCACTGGCTG GGGCTTGGTC ATGGGCCATC AGCGCATGCG TGGAACCTTT
              101 GTGGCTCCTC TGCCGATCCA TACTGCGGAA CTCCTAGCAG CTTGTTTTGC
              151 TCGCAGCCGG TCTGGAGCAA AACTTATCGG AACTGACAAT TCTGTCGTCC
              201 TCTCTCGGAA ATATACATCT TTTCCATGGC TGCTAGGTTG TGCTGCCAAC
              251 TGGATACTTC GC CPREα (SEQ ID   1 GGGACGTCCT TTGTTTACGT CCCGTCGGCG CTGAATCCTG CGGACGACCC
NO: 33)        51 TTCTCGGGGC CGCTTAGGGC TCTACCGCCC TCTCATCCGT CTGCTCTTCC
              101 AACCGACTAC GGGGCGCACC TCTCTTTACG CGGTCTCCCC GTCTGTGCCT
              151 TCTCATCTGC CGGTCCGTGT GCACTTCGCT TCACCTCTGC ACGTTGCATG
              201 GAGACCACCG TGAACGCCCC ACGGAACCTG CCAAAAGTCT TGCATAAGAG
              251 GACTCTTGGA CTTTCAGCAA TGTC CPREγ (SEQ ID   1 AACAGACCTA TAGATTGGAA AGTATGTCAA AGAATTGTGG GTCTTTTGGG
NO: 34)        51 ATTTGCTGCC CCTTTTACGC AATGTGGTTA TCCTGCGTTA ATGCCATTGT
              101 ATGCATGTAT ACAAGCAAAA CAGGCTTTCA CTTTCTCGCC AACTTATAAG
              151 GCCTTTCTAA GTCAACAATA TTCGACCCTT TACCCC Wooly Monkey    1 AATCGACCTA TTGATTGGAA AGTCTGTCAG AGAATTGTTG GTTTATTGGG
(WMPRE) (SEQ   51 CTTTGTTGCT CCCTTTACAC AATGTGGATA CGCTGCTTTA ATGCCTATAT
ID NO: 35)    101 ATACATGCAT CCAAAAACAT CAGGCCTTTA CTTTCTCTCT TGTGTACAAG
              151 ACCTTTTTGA AAGATCAATA CATGCACCTT TACCCCGTTG CTAGGCAACG
              201 AGCTGGGCAC TGCCAAGTGT TTGCTGACGC AACCCCCACT GGCTGGGGCT
              251 TGGTATGTGG CAATCAGCGC ATGCGTGGTA CATTTTGTC CCCGCTGCCT
              301 ATCCATACTG CGGAACTCCT TGCAGCCTGT TTTGCTGCT GCTGGTCAGG
              351 GGCAAAACTC ATCGGCACTG ACAACGCTGT TGTGCTGTCT CGGAAGTAAC
              401 ACACTTCCCA TGGCTGCTAG GCTGTGCTGC TACCTGGATC CTGAGAGGGA
              451 CGTGCTTTGT TTACGTCCCC TCCAAGCTGA ACCCAGCGGA CGACCCTTCT
              501 CGGGGTTGTC TCGGCCTGCT GAAACCGCTG CCGCGGCTGC TGTTCCAGCC
              551 TTCCACGGGG CGCACCTCTC TCTACGCGGT CTCCCCTCCT G WMPREα (SEQ     1 AATCGACCTA TTGATTGGAA AGTCTGTCAG AGAATTGTTG GTTTATTGGG
ID NO: 36)     51 CTTTGTTGCT CCCTTTACAC AATGTGGATA CGCTGCTTTA ATGCCTATAT
              101 ATACATGCAT CCAAAAACAT CAGGCCTTTA CTTTCTCTCT TGTGTACAAG
              151 ACCTTTTTGA AAGATCAATA CATGCACCTT TACCCC WMPREβ (SEQ     1 GTTGCTAGGC AACGAGCTGG GCACTGCCAA GTGTTTGCTG ACGCAACCCC
ID NO: 37)     51 CACTGGCTGG GGCTTGGTAT GTGGCAATCA GCGCATGCGT GGTACATTTT
              101 TGTCCCCGCT GCCTATCCAT ACTGCGGAAC TCCTTGCAGC CTGTTTTGCT
              151 CGCTGCTGGT CAGGGGCAAA ACTCATCGGC ACTGACAACG CTGTTGTGCT
              201 GTCTCGGAAG TATACACACT TCCCATGGCT GCTAGGCTGT GCTGCTACCT
              251 GGATCCTGAG A WMPREγ (SEQ     1 GGGACGTGCT TTGTTTACGT CCCCTCCAAG CTGAACCCAG CGGACGACCC
ID NO: 38)     51 TTCTCGGGGT TGTCTCGGCC TGCTGAAACC GCTGCCGCGG CTGCTGTTCC
              101 AGCCTTCCAC GGGGCGCACC TCTCTCTACG CGGTCTCCCC TCCTG
```

III. Polynucleotide Constructs/Vectors

Polynucleotide constructs (or vectors) are also provided that include any chimeric PRE of the present disclosure. The vectors are useful for expressing recombinant polypeptides in eukaryotic cells (e.g., mammalian cells). The vectors can contain sequences that encode one or more gene(s) of interest (GOI). For the purposes of this disclosure, a gene of interest is also referred to as a transgene.

Transcriptional and post-transcriptional regulatory sequences and, optionally, translational regulatory sequences can be associated (i.e., operatively linked) with a gene of interest in the vector. Transcriptional regulatory sequences include, for example, promoters, enhancers and polyadenylation signals. Post-transcriptional regulatory sequences include, for example, introns and PREs. Translational regulatory sequences include, for example, ribosome-binding sites (e.g., Kozak sequences).

In certain embodiments, a multiple cloning site (MCS), also known as a "polylinker," is present in the vector to facilitate insertion of heterologous sequences. For example, a MCS can be disposed between a promoter and a polyadenylation signal, to facilitate insertion of transgene sequences. In vectors containing transgene sequences, the portion of the vector containing a promoter, transgene sequences a polyadenylation signal is denoted the "expression cassette."

Promoters active in eukaryotic cells are known in the art. Exemplary eukaryotic promoters include, for example SV40 early promoter, SV40 late promoter, cytomegalovirus major immediate early (MIE) promoter, EF1-alpha (translation elongation factor-1α subunit) promoter, Ubc (ubiquitin C) promoter, PGK (phosphoglycerate kinase) promoter, actin promoter and others. See also Boshart et al., GenBank Accession No. K03104; Uetsuki et al. (1989) *J. Biol. Chem.* 264:5791-5798; Schorpp et al. (1996) *Nucleic Acids Res.* 24:1787-1788; Hamaguchi et al. (2000) *J. Virology* 74:10778-10784; Dreos et al. (2013) *Nucleic Acids Res.* 41(D1):D157-D164 and the eukaryotic promoter database at http://epd.vital-it.ch, accessed on Jul. 16, 2014.

Enhancers can also be included on the vector. Non-limiting examples include those in CMV promoter and intron A sequences. Five embryonic stem cell (ESC) transcription factors were previously shown to occupy super-enhancers (Oct4, Sox2, Nanog, Klf4, and Esrrb), and there are many additional transcription factors that contribute to the control of ESCs. Six additional transcription factors (Nr5a2, Prdm14, Tcfcp211, Smad3, Stat3, and Tcf3) occupy both typical enhancers and super-enhancers and that all of these are enriched in super-enhancers. Any of these or further known in the art can be used herein.

Polyadenylation signals that are active in eukaryotic cells are known in the art and include, but are not limited to, the SV40 polyadenylation signal, the bovine growth hormone (BGH) polyadenylation signal and the herpes simplex virus thymidine kinase gene polyadenylation signal. The polyadenylation signal directs 3' end cleavage of pre-mRNA, polyadenylation of the pre-mRNA at the cleavage site and termination of transcription downstream of the polyadenylation signal. A core sequence AAUAAA is generally present in the polyadenylation signal. See also Cole et al. (1985) *Mol. Cell. Biol.* 5:2104-2113.

Exemplary introns that can be used in the vectors disclosed herein include the β-globin intron and the first intron of the human/mouse/rat/other species cytomegalovirus major immediate early (MIE) gene, also known as "intron A."

Additional post-transcriptional regulatory elements that can be included in the vectors of the present disclosure include, without limitation, the 5'-untranslated region of CMV MIE, the human Hsp70 gene, the SP163 sequence from the vascular endothelial growth factor (VEGF) gene, and the tripartite leader sequence associated with adenovirus late mRNAs. See, for example, Mariati et al. (2010) *Protein Expression and Purification* 69:9-15.

In further embodiments, the vectors disclosed herein contain a matrix attachment region (MAR), also known as a scaffold attachment region (SAR). MAR (opens chromatin or) and SAR sequences act, inter alia, to insulate (insulator or) the chromatin structure of adjacent sequences. Thus, in a stably transformed cell, in which heterologous sequences are often chromosomally integrated, a MAR or SAR sequence can prevent repression of transcription of a transgene that has integrated into a region of the cellular genome having a repressive chromatin structure (e.g., heterochromatin). Accordingly, inclusion of one or more MAR or SAR sequences in a vector can facilitate expression of a transgene from the vector in stably-transformed cells.

Exemplary MAR and SAR elements include those from the interferon beta gene, the chicken lysozyme gene, the interferon alpha-2 gene, the X29 gene MAR and the S4 MAR. The MAR or SAR sequences can be located at any location within the vector. In certain embodiments, MAR and/or SAR elements are located within the expression cassette upstream (in the transcriptional sense) of the gene of interest.

In certain embodiments, the vectors disclosed herein contain nucleotide sequences encoding a selection marker that functions in eukaryotic cells (i.e., a eukaryotic selection marker), such that when appropriate selection is applied, cells that do not contain the selection marker die or grow appreciably more slowly that do cells that contain the selection marker. An exemplary selection marker that functions in eukaryotic cells is the glutamine synthetase (GS) gene; selection is applied by culturing cells in medium lacking glutamine or selection with L-Methioniene Sulfoximine or both. Another exemplary selection marker that functions in eukaryotic cells is the gene encoding resistance to neomycin (neo); selection is applied by culturing cells in medium containing neomycin, Geneticine or G418. Additional selection markers include dihydrofolate reductase (DHFR, imparts resistance to methotrexate), puromycin-N-acetyl transferase (provides resistance to puromycin) and hygromycin kinase (provides resistance to hygromycin B). Yet additional selection markers that function in eukaryotic cells are known in the art.

The sequences encoding the selection marker(s) described above are operatively linked to a promoter and a polyadenylation signal. As stated above, promoters and polyadenylation signals that function in eukaryotic cells are known in the art.

In certain embodiments, a vector as disclosed herein can contain two or more expression cassettes. For example, a vector containing two expression cassettes, one of which encodes an antibody heavy chain, and the other of which encodes an antibody light chain can be used for production of functional antibody molecules.

The vectors disclosed herein also contain a replication origin that functions in prokaryotic cells (i.e., a prokaryotic replication origin). Replication origins that functions in prokaryotic cells are known in the art and include, but are not limited to, the oriC origin of *E. coli*; plasmid origins such as, for example, the pSC101 origin, the pBR322 origin (rep) and the pUC origin; and viral (i.e., bacteriophage) replication origins. Methods for identifying prokaryotic replication origins are provided, for example, in Sernova & Gelfand (2008) *Brief Bioinformatics* 9(5):376-391.

The vectors disclosed herein also contain a selection marker that functions in prokaryotic cells (i.e., a prokaryotic selection marker). Selection markers that function in prokaryotic cells are known in the art and include, for example, sequences that encode polypeptides conferring resistance to any one of ampicillin, kanamycin, chloramphenicol, or tetracycline. An example of a polypeptide conferring resistance to ampicillin (and other beta-lactam antibiotics) is the beta-lactamase (bla) enzyme. Kanamycin resistance can result from activity of the neomycin phosphotransferase gene; and chloramphenicol resistance is mediated by chloramphenicol acetyl transferase.

Exemplary transgenes include any recombinant protein or e.g., hormones (such as, for example, growth hormone) erythropoietin, antibodies, polyclonal, monoclonal antibodies (e.g., rituximab), antibody conjugates, fusion proteins (e.g., IgG-fusion proteins), interleukins, CD proteins, MHC proteins, enzymes and clotting factors. Antibody heavy chains and antibody light chains can be expressed from separate vectors, or from the same vector containing two expression cassettes.

In one embodiment, a polynucleotide or vector of the present disclosure includes, in addition to a PRE sequence of the present disclosure, one, or more or all of the following elements: (a) a reverse complement of the downstream UTR (RC-dUTR) downstream sequence (e.g., from a viral sequence), (b) a promoter (e.g., a viral promoter), (c) a untranslated region (UTR) upstream sequence (e.g., from a viral sequence), (d) an Intron A (e.g., an EF1 alpha intron, or from a viral sequence), and (e) an UTR downstream sequence (e.g., a viral 3'-UTR).

In one embodiment, the polynucleotide or vector of the present disclosure includes, in addition to a PRE sequence of the present disclosure, at least two of such elements, such as, (b) and (c), (b) and (d), (b) and (e), (a) and (b), (c) and (d), (c) and (e), or (d) and (e).

In one embodiment, the polynucleotide or vector of the present disclosure includes, in addition to a PRE sequence of the present disclosure, at least three of such elements, such as, (b), (c) and (d); (b), (c) and (e); (b), (d) and (e); (a), (b), and (c), (a), (b) and (d), (a), (b), and (e); (a), (c) and (e); (a), (c) and (d), and (a), (d) and (e).

In one embodiment, the polynucleotide or vector of the present disclosure includes, in addition to a PRE sequence of the present disclosure, at least four of such elements, such as, (a), (b), (c) and (d); (a), (b), (c) and (e); (a), (b), (d) and (e); (a), (c), (d) and (e); and (b), (c), (d) and (e).

In any of the above embodiments, a polyadenylation signal can be optionally included.

The PRE sequence can be placed at any location in the vector, but preferably at the same orientation as the gene of interest. In one aspect, the PRE sequence is at the upstream of the gene of interest. In another aspect, the PRE sequence is at the downstream of the gene of interest. In one aspect, the PRE sequence is located between the gene of interest and the polyadenylation signal. In another aspect, the PRE sequence is downstream of the polyadenylation signal. In one aspect, the PRE sequence is located between the gene of interest and the 3'-UTR. In another aspect, the PRE sequence is downstream of the 3'-UTR.

IV. Cells and Cell Culture

The present disclosure provides methods for expressing a recombinant polypeptide in a cell. The methods comprise introducing a vector as described herein into a cell and culturing the cell under conditions in which the vector is either transiently or stably maintained in the cell. Cells can be prokaryotic or eukaryotic, such as stable cell lines generated by targeted integration with CRISP/Cas9. Cultured eukaryotic cells, that can be used for expression of recombinant polypeptides, are known in the art. Such cells include fungal cells (e.g., yeast), insect cells, plant cells and mammalian cells. Accordingly, the present disclosure provides a cell comprising a vector as described herein.

Exemplary yeast cells include, but are not limited to, *Trichoderma* sp., *Pichia pastoris*, *Schizosaccharomyces pombae* and *Saccharomyces cerevisiae*. Exemplary insect cell lines include, but are not limited to, Sf9, Sf21, and *Drosophila* S2 cells. Exemplary plant cells include, but are not limited to, *Arabidopsis* cells and tobacco BY2 cells.

Cultured mammalian cell lines, useful for expression of recombinant polypeptides, include Chinese hamster ovary (CHO) cells, human embryonic kidney (HEK) cells, virally transformed HEK cells (e.g., HEK293 cells), NS0 cells, SP20 cells, CV-1 cells, baby hamster kidney (BHK) cells, 3T3 cells, Jurkat cells, HeLa cells, COS cells, PERC.6 cells, CAP® cells and CAP-T® cells (the latter two cell lines being commercially available from Cevec Pharmaceuticals, Cologne, Germany). A number of derivatives of CHO cells are also available such as, for example, CHO-DXB11, CHO-DG-44, CHO-K1, CHO-S, or engineered CHO cells such as CHO-M, CK1 SV CHO, and CHOZN. Mammalian primary cells can also be used.

In certain embodiments, the cells are cultured in a serum-free medium. For example, for manufacture of therapeutic proteins for administration to patients, expressing cells must be grown in serum-free medium. In additional embodiments, the cells have been pre-adapted for growth in serum-free medium prior to being used for polypeptide expression.

The vectors as described herein can be introduced into any of the aforementioned cells using methods that are known in the art. Such methods include, but are not limited to, polyethylene glycol (PEG)-mediated methods, electroporation, biolistic delivery (i.e., particle bombardment), protoplast fusion, DEAE-dextran-mediated methods, and calcium phosphate co-precipitation. See also, Sambrook et al. "Molecular Cloning: A Laboratory Manual," Third Edition, Cold Spring Harbor Laboratory Press, 2001; and Ausubel et al., "Current Protocols in Molecular Biology," John Wiley & Sons, New York, 1987 and periodic updates.

Standard methods for cell culture are known in the art. See, for example, R. I. Freshney "Culture of Animal Cells: A Manual of Basic Technique," Fifth Edition, Wiley, New York, 2005.

EXAMPLES

The disclosure is further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications fall within the scope of the appended claims.

Example 1. Vector for Testing PRE Sequences

In this example, the effect of different PRE sequences on mRNA levels in transfected cells was tested using a vector (pCT2.1) containing sequences encoding the light chain of the anti-CD20 antibody Rituximab.

A schematic diagram of the pCT2.1 vector is shown in FIG. 4. Upstream of the light-chain gene, the vector contained the major immediate early (MIE) promoter, 5' untranslated region and Intron A of human cytomegalovirus. Downstream of the light-chain gene, the vector contained the bovine growth hormone (BGH) polyadenylation signal. The vector also contained a prokaryotic replication origin (ori) and a marker for selection in prokaryotic cells (bla) as well as eukaryotic selection cassette. The eukaryotic selection cassette contained a selectable marker (GS/puro/DHFR/Neo) under the transcriptional control of the SV40 early promoter and a SV40 early polyadenylation signal.

Example 2: Assay System for Testing PRE Function

The effects of different PREs, modified PRES and hybrid PREs on light chain expression levels were tested by transferring Rituximab light chain-expressing, PRE-containing plasmids into CHO cells by electroporation, followed by measurement of light chain levels. For each PRE tested, the sequence of the PRE was chemically synthesized, then inserted into a BamHI site in the pCT2.1 vector located between the light-chain sequences and the BGH polyadenylation signal (see FIG. 4).

For these experiments, CHOK1 cells were adapted to serum free media and transfected using electroporation. For each transfection pMax GFP plasmid was transfected with PRE test vector with a ratio of 1:10 of each plasmid using the Gene Pulser II electoporator (BioRad, Hercules, Calif.), using the conditions recommended by the manufacturer.

Following electroporation, cells were transferred to T25 flasks or 6 well plates serum free media (Gibco/Life Technologies, Grand Island, N.Y.). After culture for 24 hours at 37° C., viable cell density (VCD) and cell viability were determined using a ViCell counter (Beckman Coulter, Indianapolis, Ind.). After 24 hrs GFP expression was measured using an AccuriC6 Reader (Becton Dickinson, Franklin Lakes, N.J.) and samples were saved for determination of Rituximab light chain levels.

Rituximab light chain levels were determined by sandwich ELISA at 24 and 48 hours after transfection. For ELISA, plates were coated with a polyclonal goat anti-human IgG capture antibody (Jackson ImmunoResearch, West Grove, Pa.). A monoclonal horseradish peroxidase (HRP)-conjugated goat anti-human kappa light chain Cat. No. AP502P (Millipore) was used as the detection antibody. For measurement of peroxidase activity, o-phenylenediamine (OPD) was used as substrate, and absorbance was measured at 480 nm using a BMG POLARStar microplate reader (MTX Lab Systems, Vienna, Va.).

Example 3: Comparison of PRE Sequences

The assay system described in Example 2 was used to test a number of different PRE sequences, as shown in Table 3. The test PRE sequences were inserted into the pCT2.1 vector (Example 1 above) at a BamHI site located between the Rituximab light-chain sequences and the BGH polyadenylation site.

Each of the plasmids was transfected into suspension and serum free media adapted CHOK1 cells by electroporation as described in Example 2, and Rituximab light-chain levels were measured at both 24 and 48 hrs hours after transfection. Light-chain expression was normalized among the different samples by dividing the antibody levels obtained from the ELISA assay by mean fluorescence intensity of GFP; and the normalized light-chain expression levels were measured.

Table 7 shows the subelement structure of PREs tested in the examples.

TABLE 7

| Construct | PREs tested in the examples ("—" indicates absence of the subelement) | | |
|---|---|---|---|
| | γ | α | β |
| 2.1 (Control) | — | — | — |
| 2.0 (WPRE) | WPRE | WPRE | WPRE |
| 2.10 (ASPRE) | ASPRE | ASPRE | ASPRE |
| 2.21 | — | BPRE | HPRE |
| 2.22 | — | BPRE* | HPRE |
| 2.23 | GSPRE | GSPRE | HPRE |
| 2.24 | GSPRE* | GSPRE* | HPRE |
| 2.4 | WPRE | GSPRE | GSPRE |
| 2.5 | — | WPRE | HPRE |
| 2.52 | WPRE | GSPRE | HPRE |
| 2.7 | — | HPRE | WPRE |
| 2.8 (GSPRE) | GSPRE | GSPRE | GSPRE |
| 2.9 (BPRE) | BPRE | BPRE | BPRE |

*mutated subelement

Figure 5:
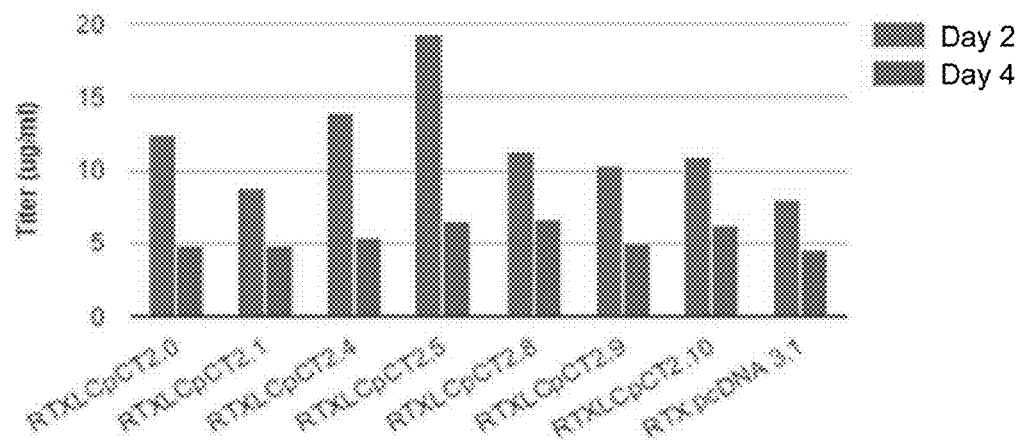
FIG. 5 shows the titer (µg/ml) in two assays (day 2 and day 4) of a few PRE constructs.

FIG. 5 shows the results of comparing a number of PRE constructs at day 2 and day 4 after transfection. Constructs 2.0 (WPRE) and 2.8 (GSPRE) are similarly potent. However, when the γ subelement in the GSPRE was replaced with the γ subelement of WPRE, the fusion construction (2.4) was 33% stronger than either WPRE or GSPRE. This demonstrates that the γ subelement of WPRE is stronger than that of the GSPRE, whereas the other subelements of GSPRE (e.g., α subelement) are likely stronger than those of WPRE.

BPRE (2.9) includes all three elements, yet BPRE is far weaker than WPRE, suggesting that being tripartite (i.e., having all three subelements) does not render a PRE element strong. Rather, its strength, to a greater extend, depends on the strength of each individual subelements. Similarly, bipartite construct 2.5 is stronger than tripartite constructs 2.8, 2.9 and 2.10.

Based on the above revelation, this example further designed constructs 2.21 (deleting BPRE's γ subelement and replacing its β subelement with that of HPRE), 2.22 (introducing a point mutation in the α subelement), 2.23 (GSPRE's β subelement replaced with that of HPRE), and 2.24 (2.23 with a point mutation in each of the γ and α subelements).

Figure 6:
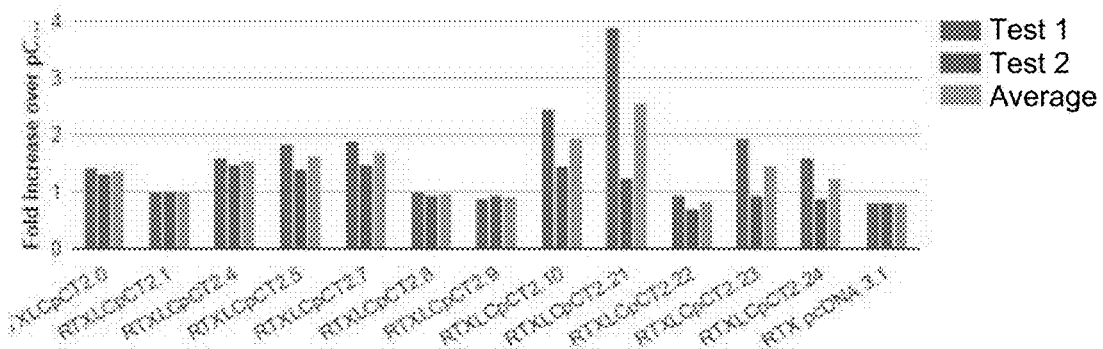
FIG. 6 shows the relative expression fold changes of a number of PRE constructs (bars: test 1, test 2, average).

The comparison is shown in FIG. 6. Constructs 2.21, 2.5, 2.6, and 2.7 are PREs that lack any γ subelement, yet are all as good as or better than the γ subelement-containing WPRE. This experiment, therefore, further confirms that the strength of a PRE element depends more on the strength of each subelement than the number of the subelements.

Figure 7A:
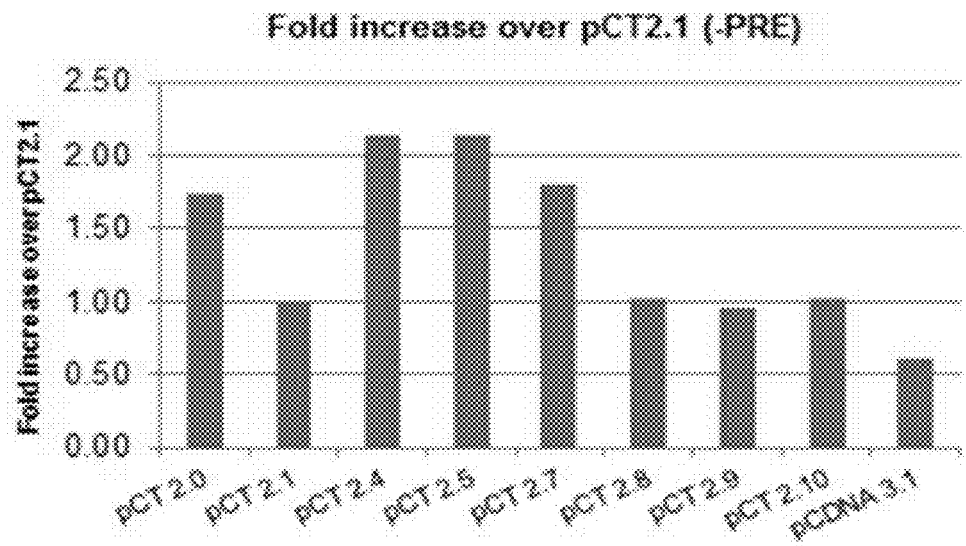
FIGS. 7A and 7B show the relative expression fold changes of a number of PRE constructs as indicated.
Figure 7B:
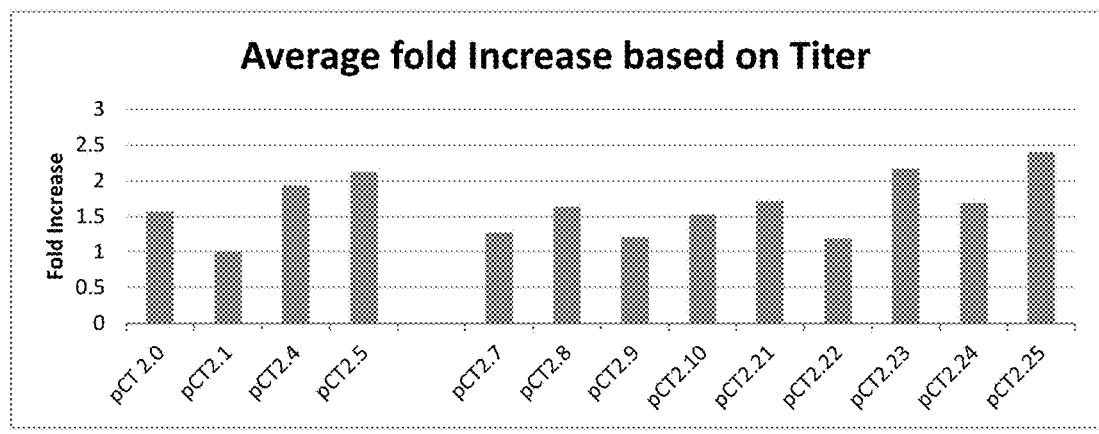

These PRE constructs were tested again with eight repeats and results are presented in FIG. 7A and FIG. 7B. The combination of BPRE α and HPRE β (2.21) was one of our highest expressors at a 72% increase in expression. However, the point mutations in the α (2.22) resulted in a construct that only produced a 19% increase in expression. Further, knocking out the α subelement of 2.21 caused the construct to be 26% as effective, suggesting the importance of the BPRE α subelement.

The replacement of GSPRE's β subelement with HPRE's subelement (2.23) resulted in a 46.6% increase in expression compared to the WPRE gamma replacement (2.4) resulting in a 33% increase in expression. Thus, HPRE's β is a stronger subelement than WPRE's γ subelement.

It was earlier believed that "the strength of the posttranscriptional effect is determined by the number of subelements in the RNA." Donello et al., J Virol. 1998 June; 72(6): 5085-5092 at 5085. Here, however, the experiments show that BPRE's alpha, HPRE's beta, and WPRE's gamma elements each as the most important pieces in the functioning of their respective molecules (2.21 vs 2.22, 2.23 vs 2.8, 2.4 vs 2.8). Contrary of the conventional understanding, therefore, the present study shows that the strength of the PRE does not depend on the number of subelements, but on the strength of each subelement.

Figure 8A:
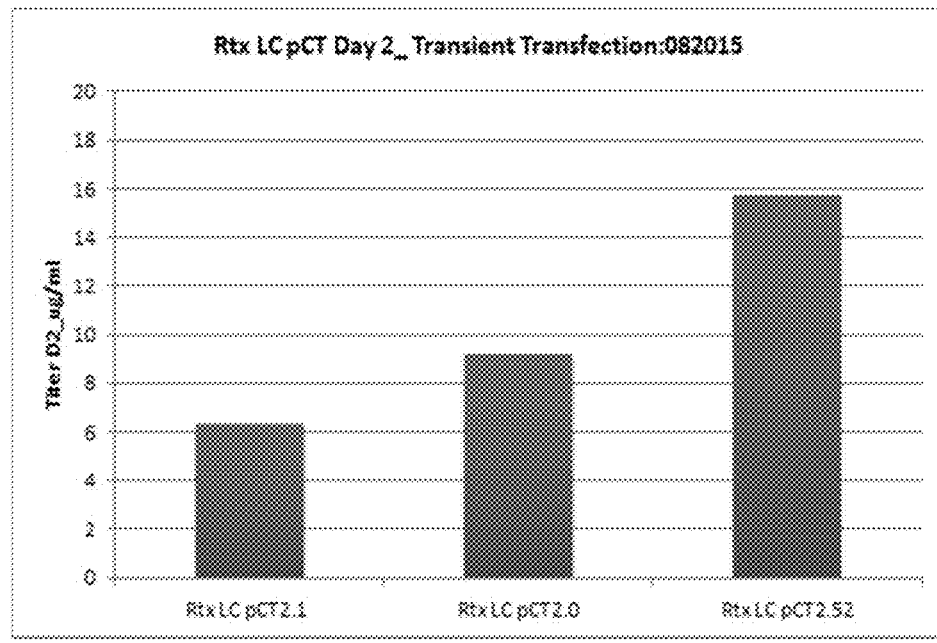
FIGS. 8A and 8B compare the strength of construct pCT 2.52 to WPRE (pCT 2.0) and control pCT2.1 at day 2 (A) and day 4 (B).
Figure 8B:
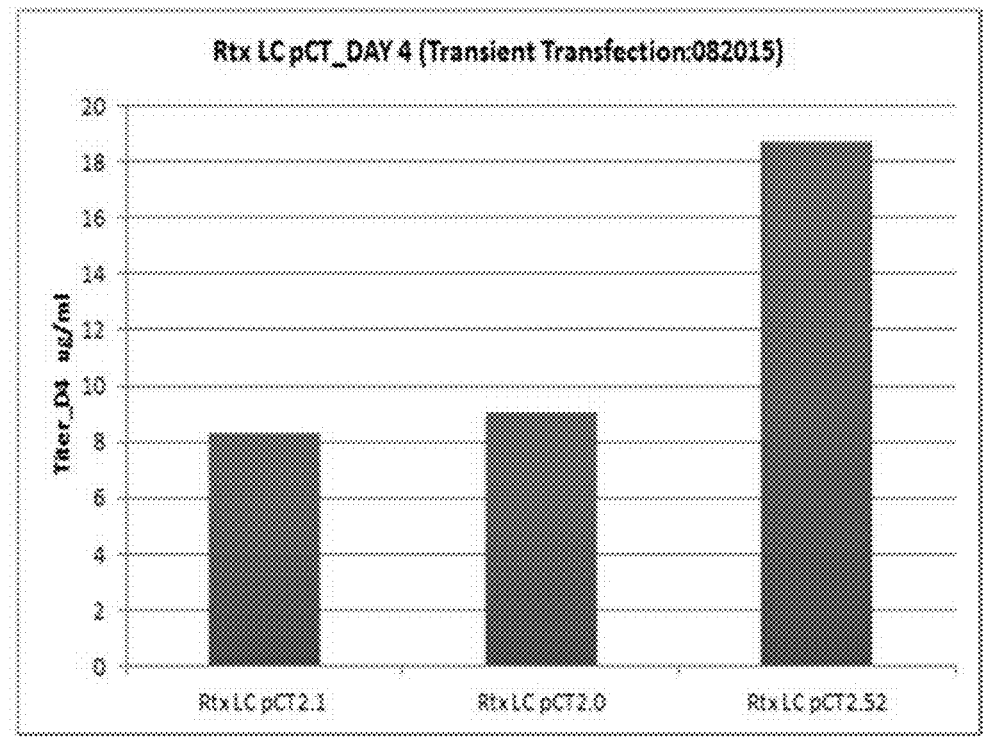

FIGS. 8A and 8B show the summary data of two experiments comparing construct 2.52 to 2.0 and 2.1. pCT 2.52 (WPRE gamma+GSPRE alpha+HPRE beta) was 2 fold stronger than 2.0 (WPRE) at day 4. It is also interesting to note that while pCT 2.0 (WPRE) loss its edge over the control over time (compare day 4 in FIG. 8B to day 2 in FIG. 8A) as expression remains constant after it tops out, the newly designed chimeric pCT2.52 PRE continued to increase in expression along with the control.

All of the PRE constructs were tested again in 8 replicates, and the final data are presented in Table 2 above.

Example 4: Interaction Between Native PRE and Other Regulatory Elements

This experiment tested the relationship between PRE and other regulatory elements. The constructs listed in Table 8 below contained the indicated promoter or other regulatory elements. In addition, constructs 2.52, 2.53, and 2.54 contained PRE subelements as shown in Table 2 for 2.52, including a γ subelement of WPRE, an α subelement of GSPRE and a β subelement from HPRE. Constructs 2.0, 2.36, 2.39 and 2.50 contained the native WPRE (i.e., γ, α and β subelements all from WPRE), and constructs 2.1, 2.32, 2.37 and 2.51 did not contain any PRE elements.

TABLE 8

Constructed tested in the example ("—" indicates absence of the element)

| Construct | RC of d-UTR | CMV Promoter | U-UTR | Intron A | d-UTR |
|---|---|---|---|---|---|
| 2.52 | Present | Present | Present | Present | Present |
| 2.53 | — | Present | Present | — | — |
| 2.54 | — | Present | — | — | — |
| 2.0/2.1 | Present | Present | Present | Present | Present |
| 2.36/2.32 | Present | Present | Present | — | — |

TABLE 8-continued

Constructed tested in the example ("—" indicates absence of the element)

| Construct | RC of d-UTR | CMV Promoter | U-UTR | Intron A | d-UTR |
|---|---|---|---|---|---|
| 2.39/2.37 | Present | Present | — | — | — |
| 2.50/2.51 | — | Present | — | — | — |

Figure 9A:
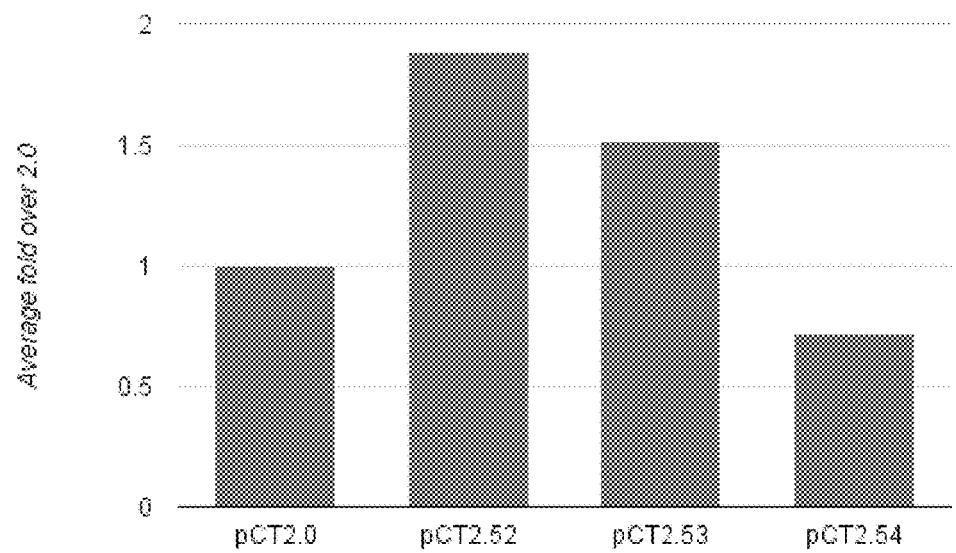
FIGS. 9A and 9B show the relative transient expression fold changes for each indicated construct.
Figure 9B:
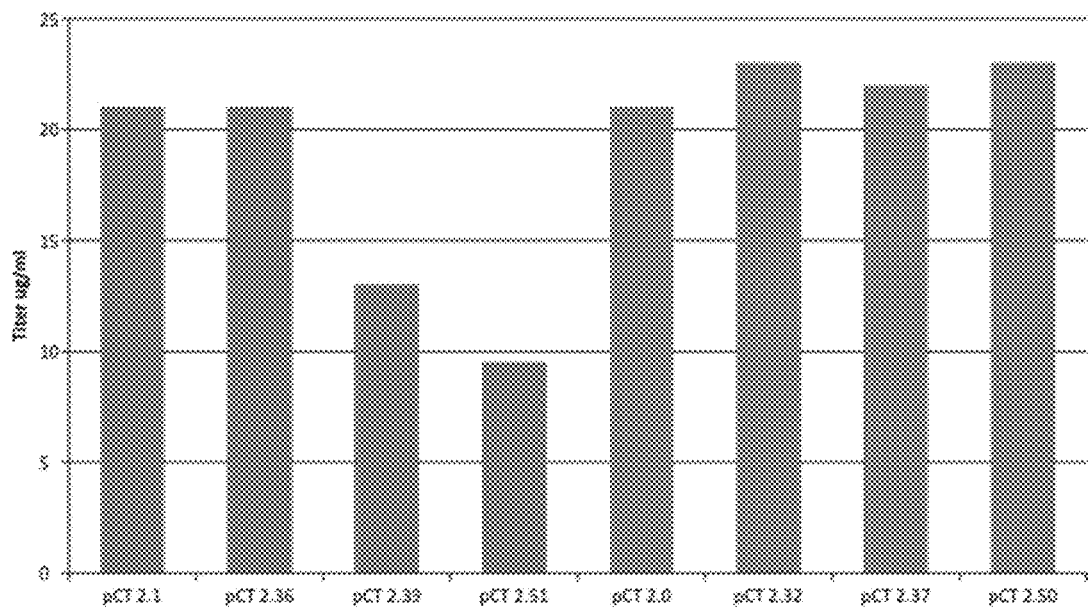

FIG. 9A shows that the effectiveness of the chimeric PRE of construct 2.52 (i.e., γ subelement of WPRE, α subelement of GSPRE and β subelement from HPRE) decreased when RC-dUTR, U-UTR, Intron A, and/or d-UTR were removed from the construct. Surprisingly, such removal did not show a marked negative effect for WPRE (compare constructs 2.0, 2.32, 2.37 and 2.50 in FIG. 9B). As control, when no PRE elements were used, the removal of these additional regulatory elements did have negative impacts (see left half of FIG. 9B).

This experiment, therefore, suggests that the native WPRE element did not benefit from the presence of one or more of the additional regulatory elements, RC-dUTR, U-UTR, Intron A, or d-UTR. It is contemplated that the native WPRE and one or more of these regulatory elements may have redundant functions. Other types of interactions between the one or more of these regulatory elements and the native WPRE element are also possible. Such non-productive interactions were not observed with the chimeric PRE elements tested, further underscoring the unexpected advantages of such chimeric PRE elements.

It is to be understood that while the invention has been described in conjunction with the above embodiments, that the foregoing description and examples are intended to illustrate and not limit the scope of the invention. Other aspects, advantages and modifications within the scope of the invention will be apparent to those skilled in the art to which the invention pertains.

What is claimed is:

1. A polynucleotide comprising:
   (a) a first fragment consisting of the nucleic acid sequence of SEQ ID NO: 7 or a nucleic acid sequence having at least 95% sequence identity to SEQ ID NO: 7,
   (b) a second fragment consisting of the nucleic acid sequence of SEQ ID NO: 9 or a nucleic acid sequence having at least 95% sequence identity to SEQ ID NO: 9, and
   (c) a third fragment consisting of the nucleic acid sequence of SEQ ID NO: 3 or a nucleic acid sequence having at least 95% sequence identity to SEQ ID NO: 3.

2. The polynucleotide of claim 1, wherein the second fragment is between the first fragment and the third fragment and each fragment is not more than 20 nucleotides away from a neighboring fragment.

3. A polynucleotide construct, comprising the polynucleotide of claim 1 and a protein-coding sequence.

4. The polynucleotide construct of claim 3, further comprising a 3'-UTR.

5. The polynucleotide construct of claim 3, further comprising a poly(A) sequence.

6. A cell, in culture, comprising the polynucleotide construct of claim 3.

* * * * *

SEQUENCE LISTING

```
<160> NUMBER OF SEQ ID NOS: 44

<210> SEQ ID NO 1
<211> LENGTH: 722
<212> TYPE: DNA
<213> ORGANISM: Hepatitis B virus

<400> SEQUENCE: 1
aaacaggcct attgattgga aagtttgtca acgaattgtg ggtcttttgg ggtttgctgc      60
cccttttacg caatgtggat atcctgcttt aatgccttta tatgcatgta tacaagcaaa     120
acaggctttt actttctcgc caacttacaa ggcctttctc agtaaacagt atatgaccct     180
ttaccccgtt gctcggcaac ggcctggtct gtgccaagtg tttgctgacg caaccccccac     240 tggttggggc ttggccatag gccatcagcg catgcgtgga acctttgtgt ctcctctgcc     300
gatccatact gcggaactcc tagccgcttg ttttgctcgc agcaggtctg gagcaaacct     360
catcgggacc gacaattctg tcgtactctc ccgcaagtat acatcgtttc catggctgct     420
aggctgtgct gccaactggt acctgcgcgg gacgtccttt gtttacgtcc cgtcggcgct     480
gaatcccgcg gacgaccct cccggggccg cttgggctc taccgcccgc ttctccgtct       540
gccgtaccgt ccgaccacgg ggcgcacctc tctttacgcg gactccccgt ctgtgccttc     600
tcatctgccg gaccgtgtgc acttcgcttc acctctgcac gtcgcatgga gaccaccgtg     660
```

```
aacgcccacc ggaacctgcc caaggtcttg cataagagga ctcttggact ttcagcaatg    720
tc                                                                   722

<210> SEQ ID NO 2
<211> LENGTH: 261
<212> TYPE: DNA
<213> ORGANISM: Hepatitis B virus

<400> SEQUENCE: 2
gttgctcggc aacggcctgg tctgtgccaa gtgtttgctg acgcaacccc cactggttgg    60
ggcttggcca taggccatca gcgcatgcgt ggaacctttg tgtctcctct gccgatccat   120
actgcggaac tcctagccgc ttgttttgct cgcagcaggt ctggagcaaa cctcatcggg   180
accgacaatt ctgtcgtact ctcccgcaag tatacatcgt ttccatggct gctaggctgt   240
gctgccaact ggtacctgcg c                                             261

<210> SEQ ID NO 3
<211> LENGTH: 172
<212> TYPE: DNA
<213> ORGANISM: Hepatitis B virus

<400> SEQUENCE: 3
gggacgtcct tgtttacgt cccgtcggcg ctgaatcccg cggacgaccc ctcccggggc    60
cgcttggggc tctaccgccc gcttctccgt ctgccgtacc gtccgaccac ggggcgcacc   120
tctctttacg cggactcccc gtctgtgcct tctcatctgc cggaccgtgt gc           172

<210> SEQ ID NO 4
<211> LENGTH: 602
<212> TYPE: DNA
<213> ORGANISM: Woodchuck hepatitis virus

<400> SEQUENCE: 4
gatccaatca acctctggat tacaaaattt gtgaaagatt gactggtatt cttaactatg    60
ttgctccttt tacgctatgt ggatacgctg ctttaatgcc tttgtatcat gctattgctt   120
cccgtatggc tttcattttc tcctccttgt ataaatcctg gttgctgtct ctttatgagg   180
agttgtggcc cgttgtcagg caacgtggcg tggtgtgcac tgtgtttgct gacgcaaccc   240
ccactggttg gggcattgcc accacctgtc agctcctttc cgggactttc gctttccccc   300
tccctattgc cacggcggaa ctcatcgccg cctgccttgc ccgctgctgg acagggctc   360 ggctgttggg cactgacaat tccgtggtgt tgtcggggaa gctgacgtcc tttccatggc   420
tgctcgcctg tgttgccacc tggattctgc gcgggacgtc cttctgctac gtcccttcgg   480
ccctcaatcc agcggacctt ccttcccgcg gcctgctgcc ggctctgcgg cctcttccgc   540
gtcttcgcct tcgccctcag acgagtcgga tctccctttg ggccgcctcc ccgcctggga   600
tc                                                                   602

<210> SEQ ID NO 5
<211> LENGTH: 261
<212> TYPE: DNA
<213> ORGANISM: Woodchuck hepatitis virus

<400> SEQUENCE: 5
gttgtcaggc aacgtggcgt ggtgtgcact gtgtttgctg acgcaacccc cactggttgg    60
ggcattgcca ccacctgtca gctcctttcc gggactttcg ctttccccct ccctattgcc   120
```

-continued

```
acggcggaac tcatcgccgc ctgccttgcc cgctgctgga caggggctcg gctgttgggc    180
actgacaatt ccgtggtgtt gtcggggaag ctgacgtcct ttccatggct gctcgcctgt    240
gttgccacct ggattctgcg c                                              261

<210> SEQ ID NO 6
<211> LENGTH: 150
<212> TYPE: DNA
<213> ORGANISM: Woodchuck hepatitis virus

<400> SEQUENCE: 6
gggacgtcct tctgctacgt cccttcggcc ctcaatccag cggaccttcc ttcccgcggc     60
ctgctgccgg ctctgcggcc tcttccgcgt cttcgccttc gccctcagac gagtcggatc    120
tccctttggg ccgcctcccc gcctgggatc                                     150

<210> SEQ ID NO 7
<211> LENGTH: 186
<212> TYPE: DNA
<213> ORGANISM: Woodchuck hepatitis virus

<400> SEQUENCE: 7
aatcaacctc tggattacaa aatttgtgaa agattgactg gtattcttaa ctatgttgct     60
ccttttacgc tatgtggata cgctgcttta atgcctttgt atcatgctat tgcttcccgt    120
atggctttca ttttctcctc cttgtataaa tcctggttgc tgtctcttta tgaggagttg    180
tggccc                                                               186

<210> SEQ ID NO 8
<211> LENGTH: 598
<212> TYPE: DNA
<213> ORGANISM: Bat hepatitis virus

<400> SEQUENCE: 8
aacaagcctt tggattggaa aatccttcag cgcattacgg gtctcctggg gtttcttgca     60
cccttcacga cctgtggcta tccagcccta atgcctttgt accatgccat tacccggcgc    120
caggccttaa aaatttcctg gccctttaag acctttcttt acagcctgta caagcaacct    180
ttgcccgtta tcaggcagaa gcgggcaatc tgccaggtgt ttgctgacgc aacccccact    240
ggttggggcc tggttaatca ttcctccgca tggttgcgca ggggacggtt tccccgcccc    300
ttgcctatcc attgcgcgga acttattgcc gcctgccttg ctcgccgctg gacgggagct    360
cgggttattg gaactgacaa ttccattgtg gcttcgggaa agcggacatc tttcccatgg    420
ctgctcggct gcgttgccaa ctggatgctt cggggaacgt cgttctgctt cgtcccctct    480
gcattgaatc cggcggacgc cccgtcgcgc ggactgctcg gcattcccgt cgcgccgccg    540
cctctcccgt tccgaccttc tacgggccgc acgtcactct tcgccgtctc cccatctg      598

<210> SEQ ID NO 9
<211> LENGTH: 269
<212> TYPE: DNA
<213> ORGANISM: Bat hepatitis virus

<400> SEQUENCE: 9
gttatcaggc agaagcgggc aatctgccag gtgtttgctg acgcaacccc cactggttgg     60
ggcctggtta atcattcctc cgcatggttg cgcaggggac ggtttccccg ccccttgcct    120
atccattgcg cggaacttat tgccgcctgc cttgctcgcc gctggacggg agctcgggtt    180
attggaactg acaattccat tgtggcttcg ggaaagcgga catctttccc atggctgctc    240
```
ggctgcgttg ccaactggat gcttcgggc 269

<210> SEQ ID NO 10
<211> LENGTH: 269
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 10
gttatcaggc agaagcgggc aatctgccag gtgtttgctg acggaacccc cactggttgg 60
ggcctggtta atcattcctc cgcatggttc cgcaggggac ggtttccccg ccccttgcct 120
atccattgcg cggaacttat tgccgcctgc cttgctcgcc gctggacggg agctcgggtt 180
attggaactg acaattccat tgtggcttcg ggaaagcgga catctttccc atggctgctc 240
ggctgcgttg ccaactggat gcttcgggc 269

<210> SEQ ID NO 11
<211> LENGTH: 144
<212> TYPE: DNA
<213> ORGANISM: Bat hepatitis virus

<400> SEQUENCE: 11
gaacgtcgtt ctgcttcgtc ccctctgcat tgaatccggc ggacgccccg tcgcgcggac 60
tgctcggcat tcccgtcgcg ccgccgcctc tcccgttccg accttctacg ggccgcacgt 120
cactcttcgc cgtctcccca tctg 144

<210> SEQ ID NO 12
<211> LENGTH: 186
<212> TYPE: DNA
<213> ORGANISM: Bat hepatitis virus

<400> SEQUENCE: 12
aacaagcctt tggattggaa aatccttcag cgcattacgg gtctcctggg gtttcttgca 60
cccttcacga cctgtggcta tccagcccta atgcctttgt accatgccat tacccggcgc 120
caggccttaa aaatttcctg gccctttaag acctttcttt acagcctgta caagcaacct 180
ttgccc 186

<210> SEQ ID NO 13
<211> LENGTH: 592
<212> TYPE: DNA
<213> ORGANISM: Ground squirrel hepatitis virus

<400> SEQUENCE: 13
aatcaaccct tagattataa aatatgtgaa aggttgacgg gcattcttaa ttatgttgct 60
ccttttacca aatgtggtta tgctgcttta ctgcctttat atcaagctat tgcttctcat 120
actgcttttg ttttctcctc cttatataaa aactggttac tgtcacttta tggtgagttg 180
tggcccgttg ccagacaacg tggtgtggtg tgctctgtgt ttgctgacgc aactcccact 240
ggttggggca tttgcaccac ctgtcaactc atttccggta ctttcggttt ctcacttccg 300
attgctaccg cggagcttat agccgcctgc cttgctcgct gctggacagg agctcggttg 360
ttgggcactg ataactccgt ggtcctctcc ggtaagctaa cttcgtttcc atggctgctc 420
gcctgtgttg ccaactggat tcttcgcggg acgtccttct gttacgtccc ctccgcggac 480
aacccagcgg accttccgtc tcggggactt ctgccggctc tccgtcctct gccgcttctg 540

```
cgttttcgtc cggtcaccaa gcggatatcc ctgtgggccg cctccccgcc tg          592
```

<210> SEQ ID NO 14
<211> LENGTH: 261
<212> TYPE: DNA
<213> ORGANISM: Ground squirrel hepatitis virus

<400> SEQUENCE: 14

```
gttgccagac aacgtggtgt ggtgtgctct gtgtttgctg acgcaactcc cactggttgg   60
ggcatttgca ccacctgtca actcatttcc ggtactttcg gtttctcact tccgattgct  120
accgcggagc ttatagccgc ctgccttgct cgctgctgga caggagctcg gttgttgggc  180
actgataact ccgtggtcct ctccggtaag ctaacttcgt ttccatggct gctcgcctgt  240
gttgccaact ggattcttcg c                                            261
```

<210> SEQ ID NO 15
<211> LENGTH: 145
<212> TYPE: DNA
<213> ORGANISM: Ground squirrel hepatitis virus

<400> SEQUENCE: 15

```
gggacgtcct tctgttacgt cccctccgcg acaacccag cggaccttcc gtctcgggga    60
cttctgccgg ctctccgtcc tctgccgctt ctgcgttttc gtccggtcac caagcggata  120
tccctgtggg ccgcctcccc gcctg                                        145
```

<210> SEQ ID NO 16
<211> LENGTH: 186
<212> TYPE: DNA
<213> ORGANISM: Ground squirrel hepatitis virus

<400> SEQUENCE: 16

```
aatcaaccct tagattataa atatgtgaa aggttgacgg gcattcttaa ttatgttgct    60
ccttttacca aatgtggtta tgctgcttta ctgcctttat atcaagctat gcttctcat   120
actgcttttg ttttctcctc cttatataaa aactggttac tgtcacttta tggtgagttg  180
tggccc                                                             186
```

<210> SEQ ID NO 17
<211> LENGTH: 582
<212> TYPE: DNA
<213> ORGANISM: Arctic ground squirrel hepatitis B virus

<400> SEQUENCE: 17

```
aacctttaga ttataaaatc tgtgaaaggt taacaggcat tctgaattat gttgctcctt    60
ttactaaatg tggttatgct gctctccttc ctttgtatca agctacttcg cgtacggcat   120
ttgtgttttc ttctctctac cacagctggt tgctgtccct ttatgctgag ttgtggcctg   180
ttgccaggca acgtggcgtg gtgtgctctg tgtctgacgc aacccccact ggttgggca   240
tttgcaccac ctatcaactc atttccccga cgggcgcttt tgccctgccg atcgccaccg   300
cggacgtcat cgccgcctgc cttgctcgct gctggacagg agctcggctg ttgggcactg   360
acaactccgt ggttctttcg ggcaaactga cttcctatcc atggctgctc gcctgtgttg   420
ccaactggat tcttcgcggg acgtcgttct gctacgtccc ttcggcagcg aatccggcgg   480
acctgccgtc tcgaggcctt ctgccggctc tgcatcccgt gccgactctc gcttccgtc    540
cgcagctgag tcgcatctcc ctttgggccg cctccccgcc tg                      582
```

<210> SEQ ID NO 18
<211> LENGTH: 258
<212> TYPE: DNA
<213> ORGANISM: Arctic ground squirrel hepatitis B virus

<400> SEQUENCE: 18
gttgccaggc aacgtggcgt ggtgtgctct gtgtctgacg caaccccac tggttggggc    60 atttgcacca cctatcaact catttccccg acgggcgctt ttgccctgcc gatcgccacc   120
gcggacgtca tcgccgcctg ccttgctcgc tgctggacag gagctcggct gttgggcact   180
gacaactccg tggttctttc gggcaaactg acttcctatc catggctgct cgcctgtgtt   240
gccaactgga ttcttcgc                                                 258

<210> SEQ ID NO 19
<211> LENGTH: 145
<212> TYPE: DNA
<213> ORGANISM: Arctic ground squirrel hepatitis B virus

<400> SEQUENCE: 19
gggacgtcgt tctgctacgt cccttcggca gcgaatccgg cggacctgcc gtctcgaggc    60
cttctgccgg ctctgcatcc cgtgccgact ctccgcttcc gtccgcagct gagtcgcatc   120 tcccttggg ccgcctcccc gcctg                                         145

<210> SEQ ID NO 20
<211> LENGTH: 179
<212> TYPE: DNA
<213> ORGANISM: Arctic ground squirrel hepatitis B virus

<400> SEQUENCE: 20
aacctttaga ttataaaatc tgtgaaaggt taacaggcat tctgaattat gttgctcctt    60
ttactaaatg tggttatgct gctctccttc ctttgtatca agctacttcg cgtacggcat   120
ttgtgttttc ttctctctac cacagctggt tgctgtccct ttatgctgag ttgtggcct    179

<210> SEQ ID NO 21
<211> LENGTH: 592
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
aatcaacctc tggattacaa aatttgtgaa agattgactg gtattcttaa ctatgttgct    60
ccttttacgc tatgtggata cgctgcttta atgcctttgt atcatgctat tgcttcccgt   120
atggctttca ttttctcctc cttgtataaa tcctggttgc tgtctctta tgaggagttg   180 tggcccgttg ccagacaacg tggtgtggtg tgctctgtgt ttgctgacgc aactcccact   240
ggttggggca tttgcaccac ctgtcaactc atttccggta ctttcggttt ctcacttccg   300
attgctaccg cggagcttat agccgcctgc cttgctcgct gctggacagg agctcggttg   360
ttgggcactg ataactccgt ggtcctctcc ggtaagctaa cttcgtttcc atggctgctc   420
gcctgtgttg ccaactggat tcttcgcggg acgtccttct gttacgtccc ctccgcggac   480
aacccagcgg accttccgtc tcggggactt ctgccggctc tcgtcctct gccgcttctg   540 cgttttcgtc cggtcaccaa gcggatatcc ctgtgggccg cctccccgcc tg           592

<210> SEQ ID NO 22

```
<211> LENGTH: 411
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gttgctcggc aacggcctgg tctgtgccaa gtgtttgctg acgcaacccc cactggttgg      60
ggcttggcca taggccatca gcgcatgcgt ggaacctttg tgtctcctct gccgatccat     120
actgcggaac tcctagccgc ttgttttgct cgcagcaggt ctggagcaaa cctcatcggg     180
accgacaatt ctgtcgtact ctcccgcaag tatacatcgt ttccatggct gctaggctgt     240
gctgccaact ggtacctgcg cgggacgtcc ttctgctacg tcccttcggc cctcaatcca     300
gcggaccttc cttcccgcgg cctgctgccg gctctgcggc ctcttccgcg tcttcgcctt     360
cgccctcaga cgagtcggat ctcccttTgg gccgcctccc cgcctgggat c              411

<210> SEQ ID NO 23
<211> LENGTH: 543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 23
gttatcaggc agaagcgggc aatctgccag gtgtttgctg acgcaacccc cactggttgg      60
ggcctggtta atcattcctc cgcatggttg cgcaggggac ggtttccccg ccccttgcct     120
atccattgcg cggaacttat tgccgcctgc cttgctcgcc gctggacggg agctcgggtt     180
attggaactg acaattccat tgtggcttcg ggaaagcgga catctttccc atggctgctc     240
ggctgcgttg ccaactggat gcttcgggcg ggacgtcctt tgtttacgtc ccgtcggcgc     300
tgaatcccgc ggacgacccc tcccggggcc gcttggggct ctaccgcccg cttctccgtc     360
tgccgtaccg tccgaccacg gggcgcacct ctctttacgc ggactccccg tctgtgcctt     420
ctcatctgcc ggaccgtgtg cacttcgctt cacctctgca cgtcgcatgg agaccaccgt     480
gaacgcccac cggaacctgc ccaaggtctt gcataagagg actcttggac tttcagcaat     540
gtc                                                                  543

<210> SEQ ID NO 24
<211> LENGTH: 543
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 24
gttatcaggc agaagcgggc aatctgccag gtgtttgctg acggaacccc cactggttgg      60
ggcctggtta atcattcctc cgcatggttc cgcaggggac ggtttccccg ccccttgcct     120
atccattgcg cggaacttat tgccgcctgc cttgctcgcc gctggacggg agctcgggtt     180
attggaactg acaattccat tgtggcttcg ggaaagcgga catctttccc atggctgctc     240
ggctgcgttg ccaactggat gcttcgggcg ggacgtcctt tgtttacgtc ccgtcggcgc     300
tgaatcccgc ggacgacccc tcccggggcc gcttggggct ctaccgcccg cttctccgtc     360
tgccgtaccg tccgaccacg gggcgcacct ctctttacgc ggactccccg tctgtgcctt     420
```

| | |
|---|---|
| ctcatctgcc ggaccgtgtg cacttcgctt cacctctgca cgtcgcatgg agaccaccgt | 480 |
| gaacgcccac cggaacctgc ccaaggtctt gcataagagg actcttggac tttcagcaat | 540 |
| gtc | 543 |

<210> SEQ ID NO 25
<211> LENGTH: 722
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

| | |
|---|---|
| aatcaaccct tagattataa aatatgtgaa aggttgacgg gcattcttaa ttatgttgct | 60 |
| cctttacca aatgtggtta tgctgcttta ctgcctttat atcaagctat tgcttctcat | 120 |
| actgcttttg ttttctcctc cttatataaa aactggttac tgtcactttt tggtgagttg | 180 |
| tggcccgttg ccagacaacg tggtgtggtg tgctctgtgt ttgctgacgc aactcccact | 240 |
| ggttggggca tttgcaccac ctgtcaactc atttccggta cttttcggttt tctcacttccg | 300 |
| attgctaccg cggagcttat agccgcctgc cttgctcgct gctggacagg agctcggttg | 360 |
| ttgggcactg ataactccgt ggtcctctcc ggtaagctaa cttcgttttcc atggctgctc | 420 |
| gcctgtgttg ccaactggat tcttcgccgg gacgtccttt gtttacgtcc cgtcggcgct | 480 |
| gaatcccgcg gacgacccct cccggggccg cttgggctc taccgcccgc ttctccgtct | 540 |
| gccgtaccgt ccgaccacgg ggcgcacctc tctttacgcg gactcccgt ctgtgccttc | 600 |
| tcatctgccg gaccgtgtgc acttcgcttc acctctgcac gtcgcatgga gaccaccgtg | 660 |
| aacgcccacc ggaacctgcc caaggtcttg cataagagga ctcttggact ttcagcaatg | 720 |
| tc | 722 |

<210> SEQ ID NO 26
<211> LENGTH: 726
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 26

| | |
|---|---|
| gatccaatca acctctggat tacaaaattt gtgaaagatt gactggtatt cttaactatg | 60 |
| ttgctccttt tacgctatgt ggatacgctg ctttaatgcc tttgtatcat gctattgctt | 120 |
| cccgtatggc tttcattttc tcctccttgt ataaatcctg gttgctgtct ctttatgagg | 180 |
| agttgtggcc cgttgccaga caacgtggtg tggtgtgctc tgtgtttgct gacgcaactc | 240 |
| ccactggttg gggcatttgc accacctgtc aactcatttc cggtactttc ggtttctcac | 300 |
| ttccgattgc taccgcggag cttatagccc ctgccttgc tcgctgctgg acaggagctc | 360 |
| ggttgttggg cactgataac tccgtggtcc tctccggtaa gctaacttcg tttccatggc | 420 |
| tgctcgcctg tgttgccaac tggattcttc gcggacgtc ctttgtttac gtcccgtcgg | 480 |
| cgctgaatcc cgcggacgac ccctcccggg gccgcttggg gctctaccgc ccgcttctcc | 540 |
| gtctgccgta ccgtccgacc acggggcgca cctctcttta cgcggactcc ccgtctgtgc | 600 |
| cttctcatct gccggaccgt gtgcacttcg cttcacctct gcacgtcgca tggagaccac | 660 |
| cgtgaacgcc caccggaacc tgcccaaggt cttgcataag aggactcttg gactttcagc | 720 |
| aatgtc | 726 |

<210> SEQ ID NO 27
<211> LENGTH: 561
<212> TYPE: DNA
<213> ORGANISM: Duck hepatitis B virus

<400> SEQUENCE: 27

```
aagatttgtt gggcatttga actttgtgtt accatttact aaaggtaaca ttgaaatgtt      60
aaaaccaatg tatgctgcta ttactaacaa agttaacttt agcttctctt cagcttatag     120
gactttattg tacaaattaa ctatgggtgt ttgtaaatta gccattcgac caaagtcctc     180
tgtacctttg ccacgtgtag ccacagatgc tactccaaca catggcgcaa tatcccatat     240
caccggcggg agcgcagtgt tgctttttc aaaggtcagg gatatacata tacaggaatt      300
gctgatggta tgtttagcta agataatgat taaacccaga tgtatactct ccgattctac     360
ttttgtttgc cacaaacgtt atcagacgtt accatggcat tttgctatgt ggccaaaaca     420
actgctatct cctatacagt tgtactttgt tccaagtaaa tacaatcctg ctgacggccc     480
atccaggcac agaccgcctg attggacggc tcttacatac acccctctct cgaaagcaat     540
atatattcca cataggctat g                                               561
```

<210> SEQ ID NO 28
<211> LENGTH: 256
<212> TYPE: DNA
<213> ORGANISM: Duck hepatitis B virus

<400> SEQUENCE: 28

```
gtcctctgta cctttgccac gtgtagccac agatgctact ccaacacatg gcgcaatatc      60
ccatatcacc ggcgggagcg cagtgtttgc tttttcaaag gtcagggata tacatataca     120
ggaattgctg atggtatgtt tagctaagat aatgattaaa cccagatgta tactctccga     180
ttctactttt gtttgccaca aacgttatca gacgttacca tggcattttg ctatgttggc     240
caaacaactg ctatct                                                     256
```

<210> SEQ ID NO 29
<211> LENGTH: 131
<212> TYPE: DNA
<213> ORGANISM: Duck hepatitis B virus

<400> SEQUENCE: 29

```
cctatacagt tgtactttgt tccaagtaaa tacaatcctg ctgacggccc atccaggcac      60
agaccgcctg attggacggc tcttacatac acccctctct cgaaagcaat atatattcca     120
cataggctat g                                                          131
```

<210> SEQ ID NO 30
<211> LENGTH: 174
<212> TYPE: DNA
<213> ORGANISM: Duck hepatitis B virus

<400> SEQUENCE: 30

```
aagatttgtt gggcatttga actttgtgtt accatttact aaaggtaaca ttgaaatgtt      60
aaaaccaatg tatgctgcta ttactaacaa agttaacttt agcttctctt cagcttatag     120
gactttattg tacaaattaa ctatgggtgt ttgtaaatta gccattcgac caaa           174
```

<210> SEQ ID NO 31
<211> LENGTH: 719
<212> TYPE: DNA

<210> SEQ ID NO 31
<211> LENGTH: 719
<212> TYPE: DNA
<213> ORGANISM: Hepatitis virus
<220> FEATURE:
<223> OTHER INFORMATION: Chimpanzee hepatitis virus

<400> SEQUENCE: 31

```
aacagaccta tagattggaa agtatgtcaa agaattgtgg gtcttttggg atttgctgcc      60
ccttttacgc aatgtggtta tcctgcgtta atgccattgt atgcatgtat acaagcaaaa    120
caggctttca ctttctcgcc aacttataag gcctttctaa gtcaacaata ttcgacccctt   180
taccccgttg cccggcaacg gtccggtctg tgccaagtgt ttgctgacgc aaccccact     240
ggctggggct tggtcatggg ccatcagcgc atgcgtggaa cctttgtggc tcctctgccg    300
atccatactg cggaactcct agcagcttgt tttgctcgca gccggtctgg agcaaaactt    360
atcggaactg acaattctgt cgtcctctct cggaaatata catcttttcc atggctgcta   420
ggttgtgctg ccaactggat acttcgcggg acgtcctttg tttacgtccc gtcggcgctg    480
aatcctgcgg acgacccttc tcggggccgc ttagggctct accgccctct catccgtctg    540
ctcttccaac cgactacggg gcgcacctct ctttacgcgg tctcccgctg tgccttctca    600
tctgccggtc cgtgtgcact tcgcttcacc tctgcacgtt gcatggagac caccgtgaac    660
gccccacgga acctgccaaa agtcttgcat aagaggactc ttggactttc agcaatgtc    719
```

<210> SEQ ID NO 32
<211> LENGTH: 262
<212> TYPE: DNA
<213> ORGANISM: Hepatitis virus
<220> FEATURE:
<223> OTHER INFORMATION: Chimpanzee hepatitis virus

<400> SEQUENCE: 32

```
cgttgcccgg caacggtccg gtctgtgcca agtgtttgct gacgcaaccc ccactggctg     60
gggcttggtc atgggccatc agcgcatgcg tggaaccttt gtggctcctc tgccgatcca    120
tactgcggaa ctcctagcag cttgtttttgc tcgcagccgg tctggagcaa aacttatcgg    180
aactgacaat tctgtcgtcc tctctcggaa atatacatct tttccatggc tgctaggttg    240
tgctgccaac tggatacttc gc                                             262
```

<210> SEQ ID NO 33
<211> LENGTH: 274
<212> TYPE: DNA
<213> ORGANISM: Hepatitis virus
<220> FEATURE:
<223> OTHER INFORMATION: Chimpanzee hepatitis virus

<400> SEQUENCE: 33

```
gggacgtcct tgtttacgt cccgtcggcg ctgaatcctg cggacgaccc ttctcggggc      60
cgcttagggc tctaccgccc tctcatccgt ctgctcttcc aaccgactac ggggcgcacc    120
tctctttacg cggtctcccc gtctgtgcct tctcatctgc cggtccgtgt gcacttcgct    180
tcacctctgc acgttgcatg gagaccaccg tgaacgcccc acggaacctg ccaaaagtct    240
tgcataagag gactcttgga ctttcagcaa tgtc                                274
```

<210> SEQ ID NO 34
<211> LENGTH: 186
<212> TYPE: DNA
<213> ORGANISM: Hepatitis virus
<220> FEATURE:
<223> OTHER INFORMATION: Chimpanzee hepatitis virus

<400> SEQUENCE: 34

```
aacagaccta tagattggaa agtatgtcaa agaattgtgg gtcttttggg atttgctgcc    60
ccttttacgc aatgtggtta tcctgcgtta atgccattgt atgcatgtat acaagcaaaa   120
caggctttca ctttctcgcc aacttataag gcctttctaa gtcaacaata ttcgaccctt   180
tacccc                                                               186
```

```
<210> SEQ ID NO 35
<211> LENGTH: 591
<212> TYPE: DNA
<213> ORGANISM: Woolly monkey hepatitis B virus

<400> SEQUENCE: 35
```

```
aatcgaccta ttgattggaa agtctgtcag agaattgttg gtttattggg ctttgttgct    60 cccttttacac aatgtggata cgctgcttta atgcctatat atacatgcat ccaaaaacat  120
caggccttta ctttctctct tgtgtacaag acctttttga aagatcaata catgcacctt   180
taccccgttg ctaggcaacg agctgggcac tgccaagtgt ttgctgacgc aaccccccact 240 ggctggggct tggtatgtgg caatcagcgc atgcgtggta catttttgtc cccgctgcct   300
atccatactg cggaactcct tgcagcctgt tttgctcgct gctggtcagg gcaaaaactc   360
atcggcactg acaacgctgt tgtgctgtct cggaagtaac acacttccca tggctgctag   420
gctgtgctgc tacctggatc ctgagaggga cgtgctttgt ttacgtcccc tccaagctga   480
acccagcgga cgacccttct cggggttgtc tcggcctgct gaaaccgctg ccgcggctgc   540
tgttccagcc ttccacgggg cgcacctctc tctacgcggt ctcccctcct g            591
```

```
<210> SEQ ID NO 36
<211> LENGTH: 186
<212> TYPE: DNA
<213> ORGANISM: Woolly monkey hepatitis B virus

<400> SEQUENCE: 36
```

```
aatcgaccta ttgattggaa agtctgtcag agaattgttg gtttattggg ctttgttgct    60 cccttttacac aatgtggata cgctgcttta atgcctatat atacatgcat ccaaaaacat  120
caggccttta ctttctctct tgtgtacaag acctttttga aagatcaata catgcacctt   180
tacccc                                                               186
```

```
<210> SEQ ID NO 37
<211> LENGTH: 261
<212> TYPE: DNA
<213> ORGANISM: Woolly monkey hepatitis B virus

<400> SEQUENCE: 37
```

```
gttgctaggc aacgagctgg gcactgccaa gtgtttgctg acgcaacccc cactggctgg    60
ggcttggtat gtggcaatca gcgcatgcgt ggtacatttt tgtccccgct gcctatccat   120
actgcggaac tccttgcagc ctgttttgct cgctgctggt cagggcaaaa actcatcggc   180
actgacaacg ctgttgtgct gtctcggaag tatacacact tcccatggct gctaggctgt   240
gctgctacct ggatcctgag a                                             261
```

```
<210> SEQ ID NO 38
<211> LENGTH: 145
<212> TYPE: DNA
<213> ORGANISM: Woolly monkey hepatitis B virus

<400> SEQUENCE: 38
```

```
gggacgtgct tgtttacgt cccctccaag ctgaacccag cggacgaccc ttctcggggt      60
tgtctcggcc tgctgaaacc gctgccgcgg ctgctgttcc agccttccac ggggcgcacc     120
tctctctacg cggtctcccc tcctg                                          145

<210> SEQ ID NO 39
<211> LENGTH: 433
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 39
gttgtcaggc aacgtggcgt ggtgtgcact gtgtttgctg acgcaacccc cactggttgg      60
ggcattgcca ccacctgtca gctcctttcc gggactttcg ctttccccct ccctattgcc    120
acggcggaac tcatcgccgc ctgccttgcc cgctgctgga caggggctcg gctgttgggc    180
actgacaatt ccgtggtgtt gtcggggaag ctgacgtcct ttccatggct gctcgcctgt    240
gttgccacct ggattctgcg cgggacgtcc tttgtttacg tcccgtcggc gctgaatccc    300
gcggacgacc cctcccgggg ccgcttgggg ctctaccgcc cgcttctccg tctgccgtac    360
cgtccgacca cggggcgcac ctctctttac gcggactccc cgtctgtgcc ttctcatctg    420
ccggaccgtg tgc                                                       433

<210> SEQ ID NO 40
<211> LENGTH: 261
<212> TYPE: DNA
<213> ORGANISM: Hepatitis B virus

<400> SEQUENCE: 40
gttgctcggc aacggcctgg tctgtgccaa gtgtttgctg acgcaacccc cactggttgg      60
ggcttggcca taggccatca gcgcatgcgt ggaacctttg tgtctcctct gccgatccat    120
actgcggaac tcctagccgc ttgttttgct cgcagcaggt ctggagcaaa cctcatcggg    180
accgacaatt ctgtcgtact ctcccgcaag tatacatcgt ttccatggct gctaggctgt    240
gctgccaact ggtacctgcg c                                              261

<210> SEQ ID NO 41
<211> LENGTH: 269
<212> TYPE: DNA
<213> ORGANISM: Bat hepatitis virus

<400> SEQUENCE: 41
gttatcaggc agaagcgggc aatctgccag gtgtttgctg acgcaacccc cactggttgg      60
ggcctggtta atcattcctc cgcatggttg cgcaggggac ggtttccccg ccccttgcct    120
atccattgcg cggaacttat tgccgcctgc cttgctcgcc gctggacggg agctcgggtt    180 attgaactg acaattccat tgtggcttcg ggaaagcgga catctttccc atggctgctc    240
ggctgcgttg ccaactggat gcttcgggc                                      269

<210> SEQ ID NO 42
<211> LENGTH: 258
<212> TYPE: DNA
<213> ORGANISM: Arctic ground squirrel hepatitis B virus

<400> SEQUENCE: 42
gttgccaggc aacgtggcgt ggtgtgctct gtgtctgacg caaccccac tggttggggc      60
```

-continued

```
atttgcacca cctatcaact catttccccg acgggcgctt ttgccctgcc gatcgccacc    120
gcggacgtca tcgccgcctg ccttgctcgc tgctggacag gagctcggct gttgggcact    180
gacaactccg tggttctttc gggcaaactg acttcctatc catggctgct cgcctgtgtt    240
gccaactgga ttcttcgc                                                  258

<210> SEQ ID NO 43
<211> LENGTH: 261
<212> TYPE: DNA
<213> ORGANISM: Woodchuck hepatitis virus

<400> SEQUENCE: 43
gttgtcaggc aacgtggcgt ggtgtgcact gtgtttgctg acgcaacccc cactggttgg     60
ggcattgcca ccacctgtca gctcctttcc gggactttcg ctttcccct ccctattgcc    120 acggcggaac tcatcgccgc ctgccttgcc cgctgctgga caggggctcg gctgttgggc    180
actgacaatt ccgtggtgtt gtcggggaag ctgacgtcct ttccatggct gctcgcctgt    240
gttgccacct ggattctgcg c                                              261

<210> SEQ ID NO 44
<211> LENGTH: 261
<212> TYPE: DNA
<213> ORGANISM: Ground squirrel hepatitis virus

<400> SEQUENCE: 44
gttgccagac aacgtggtgt ggtgtgctct gtgtttgctg acgcaactcc cactggttgg     60
ggcatttgca ccacctgtca actcatttcc ggtactttcg gtttctcact tccgattgct    120
accgcggagc ttatagccgc ctgccttgct cgctgctgga caggagctcg gttgttgggc    180
actgataact ccgtggtcct ctccggtaag ctaacttcgt ttccatggct gctcgcctgt    240
gttgccaact ggattcttcg c                                              261
```